(12) United States Patent
Eliaz et al.

(10) Patent No.: US 6,206,920 B1
(45) Date of Patent: Mar. 27, 2001

(54) COMPOSITION AND METHOD FOR FORMING BIODEGRADABLE IMPLANTS IN SITU AND USES OF THESE IMPLANTS

(75) Inventors: Rom Eliaz, Beer-Sheva; Joseph Kost, Omer, both of (IL)

(73) Assignee: Ben-Gurion University of the Negev, Beer-Sheva (IL)

( * ) Notice: Subject to any disclaimer, the term of this patent is extended or adjusted under 35 U.S.C. 154(b) by 0 days.

(21) Appl. No.: 09/180,500

(22) PCT Filed: May 8, 1997

(86) PCT No.: PCT/IL97/00154

§ 371 Date: Dec. 23, 1998

§ 102(e) Date: Dec. 23, 1998

(87) PCT Pub. No.: WO97/42987

PCT Pub. Date: Nov. 20, 1997

(30) Foreign Application Priority Data

May 13, 1996 (IL) .......................................................... 118235

(51) Int. Cl.[7] .............................. A61F 2/28; A61B 19/00
(52) U.S. Cl. .......................................... 623/16.11; 128/898
(58) Field of Search .................................. 623/16, 16.11; 128/898

(56) References Cited

U.S. PATENT DOCUMENTS

| | | | |
|---|---|---|---|
| 4,938,763 | * 7/1990 | Dunn et al. | 604/891.1 |
| 5,192,802 | * 3/1993 | Rencher | 514/535 |
| 5,696,175 | * 12/1997 | Mikos et al. | 521/61 |
| 5,885,829 | * 3/1999 | Mooney et al. | 435/325 |

OTHER PUBLICATIONS

Rudoy & Duran, Ashrae Journal, vol. 7, No. 19, pp. 19–25 (Jul. 1975).

Peck et al., Proceeding of the Fifth National Passive Solar Conference, ISES–American Section, pp. 985–389 (1979).

Reisfeld, Proceeding of The SPIE International Syposium on Optical and Optoelectronic Applied Science and Engineering, San Diego Calofornia, vol. 1328, pp. 29–39 (Jul. 8–13, 1990).

Donnadieu, Material Science and Engineering, vol. B3, pp. 185–195 (1989).

Bradle & Boehm, Proceeding of Thermal Performance of THe Exterior Envelopes of Buildings II, Ashrae/Doe Conference, Ashrae SP38, No. 1, pp. 361–379 (1982).

Ashrae Fundamentals Handbook (sl Version), Chap. 27, pp. 27. 1–*27.38 (1989).

"The Effects of Gamma Irradiation of Poly(DL–Lactide) As A Solid And In N–Methyl–2–Pyrrolidone Solutions", Lowe, et al., 1993 Atrix Laboratories.

* cited by examiner

Primary Examiner—Michael J. Milano
Assistant Examiner—Hieu Phan
(74) Attorney, Agent, or Firm—Merchant & Gould P.C.

(57) ABSTRACT

The invention discloses a composition having a mixture of a pharmaceutically, medically or veterinarily acceptable polymer, preferable a poly (lactic-co-glycolic acid) copolymer (PLGA) containing between about 10 and 100 wt. % lactic acid (LA) units, preferably between about 50 and 90 wt. % LA units, and α-(tetrahydrofuranyl)-ω-hydroxypoly(oxy-1,2-ethandiyl) (glycofurol). Methods of forming solid implants in situ in an animal body, said implants optionally comprising a drug or other biologically active agent, as well as the use of the compositions of the invention in the treatment of animal bodies, are also disclosed.

26 Claims, 29 Drawing Sheets

(a) After 16 hours (b) After 16 hours (c) After 14 days (d) After 14 days (e) After 27 days (f) After 27 days (a) After 16 hours (b) After 16 hours (c) After 14 days (d) After 27 days (e) After 27 days (f) After 32 days (a) After 16 hours (b) After 16 hours (c) After 16 hours (d) After 14 days (e) After 14 days (f) After 27 days (a) After 24 hours (b) After 24 hours (c) After 21 days (d) After 21 days (e) After 36 days (f) After 36 days (a) After 24 hours (b) After 24 hours (c) After 21 days (d) After 21 days (e) After 32 days (f) After 32 days

COMPOSITION AND METHOD FOR FORMING BIODEGRADABLE IMPLANTS IN SITU AND USES OF THESE IMPLANTS

FIELD OF THE INVENTION

This invention relates to a composition useful in the in situ formation of biodegradable polymeric implants of polymers and copolymers of lactic and glycolic acid, to a method of forming such implants in situ using the composition of the invention, to implants formed thereby, and to uses of such composition, method or implants as a space-filler, for soft or hard tissue regeneration, and for the controlled release of drugs.

BACKGROUND OF THE INVENTION

The use of biodegradable polymers in medical applications, such as sutures, staples, surgical clips, implant and drug delivery systems, is well known. A particular use is the in situ formation of biodegradable implants or inserts; in this application, the term "biodegradable implant" and "biodegradable insert" will be used interchangeably. The in situ formation of biodegradable implants is described, for example, in U.S. Pat. No. 4,938,763; Duysen et al., Pharmaceutical Research, 1994, Amer. Assoc. of Pharm. Scientists, Presentation #7575; Frank et al., Pharmaceutical Research, 1994, Amer. Assoc. of Pharm. Scientists, Presentation #2070; Dunn et al., Proc. Int. Symp. Control. Rel. Bioact. Mater., 22 (1995); Dunn et al., Portland Bone Symposium, Aug. 2–5, 1995, Portland, Oreg.; Andreopoulos, Clinical Materials 15 (1994) 89–92; Lambert & Peck, J. Controlled Release 33 (1995) 189–195; Shah et al., J. Controlled Release 27 (1993) 139–147; Shively et al., J. Controlled Release 33 (1995) 237–243; Lowe et al., 19th Ann. Mtg. Soc. Biomaterials.

Such implants serve two main purposes: as space-filling material, e.g. where tissue has been removed or where bone regeneration is required; and as a mechanism for controlled release of drugs. The advantages of forming such inserts in situ as opposed to outside the body are described in the foregoing references, and include the ability to insert the implant without resorting to surgery, as well as the capability of the implant to be formed exactly to the dimensions of the cavity being filled when space-filling is the goal of the implant.

As described in U.S. Pat. No. 4,938,763, one of the methods (the "thermoplastic system") which may be employed for the in situ formation of implants is the injection of a solution containing a water-immiscible biodegradable polymer and a water-miscible biologically compatible (non-toxic) solvent into an animal. The solvent is quickly carried away from the injection site, and the polymer left behind in the aqueous environment of the body quickly coagulates or solidifies into a solid matrix structure. If the implant is meant to serve as a drug-delivery system, then the drug is incorporated into the solution prior to injection, and is trapped in the solid matrix formed upon coagulation of the polymer. As will be appreciated by persons skilled in the art, different degrees of coagulation, and thus different rates of biodegradation and/or, if applicable, drug release, may be achieved, by varying the characteristics of the polymer or copolymer (e.g., degree of hydrophobicity or average molecular weight), the solvent, and the relative amount of each component prior to injection. The relative amount of the drug and the identity of the drug are also important factors when the implant serves as a controlled-release device.

The polymers and copolymers known in the art to be suitable for use in the "thermoplastic method" of in situ implant formation disclosed in U.S. Pat. No. 4,938,763 include poly(L-lactic acid), poly(D-lactic acid), poly(DL-lactic acid), poly(L-lactide), poly(D-lactide), poly(DL-lactide), poly(DL-lactide-co-glycolide), poly(lactic-co-glycolic) acid, polyglycolide, and polyglycolic acid. Solvents known in the art include N-methyl pyrrolidone, propylene glycol, triacetin, triethyl citrate, and dimethyl sulfoxide. As stated, it will be appreciated that the degree of coagulation of the polymer, and thus the rate of biodegradation and/or drug release, is dependent in part on the choice of solvent used. On the other hand, the ability of a given biocompatible solvent to dissolve a given biodegradable polymer, and to provide a solution that can be used in a method for the in situ formation of a biodegradable polymeric implant is, at best, unpredictable. Not every biocompatible solvent can be used with any given biodegradable polymer, and not every biodegradable polymer can be used with any given solvent to provide the desired solution for use in in situ formation of a biodegradable polymeric implant. Furthermore, in view of the fact that, ultimately, the above biocompatible solvent-biodegradable polymer containing solutions are intended for administration in humans, it is essential that such solutions be acceptable pharmacologically, i.e., that their administration will be essentially harmless to the patient. Likewise, in veterinary medicine, when such implants are to be formed in, for example, domestic animals, it is essential that the solutions administered to the animals are essentially harmless.

Accordingly, in view of the above-mentioned medical and veterinary considerations, the number of potential biocompatible solvent-biodegradable polymer combinations useful for administration to humans and/or animals for in situ biodegradable implant formation is considerably restricted. One of the drawbacks of the prior art noted above is the general failure to provide specific, harmless solutions that can be used for the in situ formation of biodegradable polymers; often, at least some of the polymers to be dissolved therewith are not suitable for human or animal administration.

Another drawback of the above prior art is that often, when a desirable solvent-polymer combination is obtained that is fit for medical and/or veterinary use, the process by which such a combination, i.e., solution, is produced is often tedious, requiring special conditions for production. For example, in the above-noted U.S. Pat. No. 4,938,763, there are described various methods for preparing some solvent-polymer combinations for use as in situ forming biodegradable implants, many of which methods require the use of catalysts, more than one solvent, high temperatures and other special conditions to provide the solvent-polymer solution to be administered.

Poly(lactic-co-glycolic acid) copolymer (PLGA) is used for injection in man and used for parenteral applications. Glycofurol ($\alpha$-(tetrahydrofuranyl)-$\omega$-hydroxypoly(oxy-1,2-ethandiyl)) is used as a solvent in parenteral products for intravenous or intramuscular injection of concentrations of up to 50% v/v; when administered parenterally to humans, quantities of glycofurol should not exceed 0.07 ml per kg of body weight per day (Handbook of Pharmaceutical Excipients, Am. Pharmac. Assoc. and Pharm. Soc. of Gr. Br., 1994). However, heretofore, there has not been described a solution useful for the in situ formation of a biodegradable implant that is comprised of a biocompatible solvent being glycofurol and a biodegradable polymer being composed of lactic acid (LA) and/or glycolic acid (LG) units, e.g. PLGA, of which both polymer and solvent have been approved for human administration, and which are compatible with each other, such that the polymer may be readily dissolved in the solvent at room temperature, without the need for other additives such as catalysts, additional solvents or the like; and which solution is useful for the in situ formation of a biodegradable implant for tissue or bone replacement, and for the controlled release of drugs.

It is therefore an object of the invention to provide a composition comprising a polymer which is PLGA containing from 10–100 wt. % lactic acid (LA) units, preferably from 50–90 wt. % LA units, and a solvent which is glycofurol for use in the formation of a biodegradable implant.

It is another object of the invention to provide a method which employs the composition of the invention in the in situ formation of a biodegradable implant.

It is yet another object of the invention to provide biodegradable polymeric implants which can be as controlled-delivery devices for drugs or other biologically active agents.

It is another object the invention to provide implants the properties of which may be manipulated so as to enable the use of said implants with both hard and soft tissues.

It is still another object of the invention to provide biodegradable polymeric implants comprising as polymer PLGA containing from 10–100 wt. % LA units, preferably 50–90 wt. % LA units, whenever prepared from the composition of the invention or by the method of the invention.

Other objects of the invention will become apparent as the description proceeds.

SUMMARY OF THE INVENTION

The present invention is based on the surprising finding that solutions of the polymer PLGA (poly(lactic-co-glycolic acid) containing from 10–100 wt. % LA units, preferably 50–90 wt. % LA units, in glycofurol ($\alpha$-(tetrahydrofuranyl)-$\omega$-hydroxypoly(oxy-1,2-ethandiyl)), optionally comprising a drug or other biological agent, may be used to form biodegradable implants in situ.

The composition of the invention comprises a mixture of a polymer which is poly(lactic-co-glycolic acid) (PLGA) containing from 10–100 wt. % LA units, preferably 50–90 wt. % LA units, and a solvent which is $\alpha$-(tetrahydrofuranyl)-$\omega$-hydroxypoly(oxy-1,2-ethandiyl) (glycofurol), optionally comprising a drug or other biologically active agent dissolved, dispersed or suspended in the mixture.

The method for in situ formation of a biodegradable implant, according to the invention, comprises the steps of:
 a—dissolving a polymer which is poly(lactic-co-glycolic acid) (PLGA) containing from 10–100 wt. % LA units, preferably 50–90 wt. % LA units, in a solvent which is $\alpha$-(tetrahydrofuranyl)-$\omega$-hydroxypoly(oxy-1,2-ethandiyl) (glycofurol) to form a liquid;
 b—administering a suitable amount of said liquid to an animal body; and
 c—allowing said glycofurol to dissipate in said animal body, whereby to produce a solid implant composed of a PLGA polymeric matrix.

Optionally, a drug or other biologically active molecule may be dissolved, dispersed or suspended in the liquid prior to, concurrent with or subsequent to said dissolution of said polymer.

The term "animal body" as used herein includes the human body.

The invention also comprises compositions comprising a mixture of $\alpha$-(tetrahydrofuranyl)-$\omega$-hydroxypoly(oxy-1,2-ethandiyl) (glycofurol) and a pharmaceutically acceptable, medically acceptable, or veterinarily acceptable polymer which is soluble in glycofurol.

Other aspects and embodiments of the invention are set forth hereinbelow, or will readily arise from the following detailed description.

DETAILED DESCRIPTION OF THE INVENTION

Figures 1, 1A:
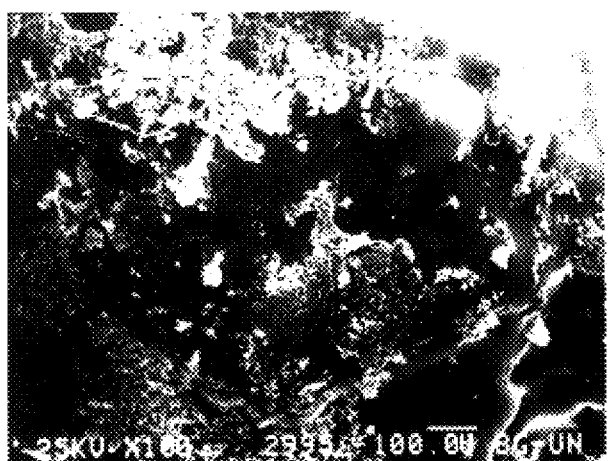
FIGS. 1A–1E show reproductions of scanning electron-micrographs of the surface of polymeric compositions formed by the method of the invention, at various periods of time after formation of each composition while each composition has been exposed to phosphate buffered solution (PBS)

Preferably, the average molecular weight of the glycofurol is between about 146.24 and 190.24. The density may be between about 1.07 and 1.09 g/cm$^3$ at 20° C.

The polymer used in the invention may range in average molecular weight from about 2000 to about 100,000. The inherent viscosity may be between about 0.2 dl/g and 7.2 dl/g.

In the compositions of the invention, the weight ratio of glycofurol to polymer may be from about 99:1 to about 1:1. Preferably, the weight ratio of glycofurol to polymer is in the range of from about 9:1 to about 7:3.

For use in the method of the invention, PLGA may be present in the liquid composition prior to administration to the animal body in a weight ratio of about 1:99 to about 1:1 relative to glycofurol. Often, good results may be obtained with PLGA in weight ratio of between about 1:9 and 3:7 relative to glycofurol.

As used herein, the term "drug" "biologically active molecule" includes any substance which is physiologically or pharmacologically active which acts locally or systemically in a body. Thus these molecules may be selected from among organic molecules, such as steroids; peptides or polypeptides; proteins, such as insulin, cytokines, their respective receptors and other therapeutic hormones and their receptors; oligo- or polynucleotides; or other biologically active molecules. The amount of biologically active molecule present in the solution prior to placement in the animal may be up to an amount equal to the weight of the polymer present prior to placement in the animal. Preferably, when a drug or biologically active molecule is incorporated into the solution, the weight ratio of the polymer to the biologically active molecule is between about 10000:1 and about 1:1.

As compositions according to the invention, the liquid compositions used in carrying out the method of the invention are part of the invention.

The invention also comprises a method of treatment of an animal in need of a prosthetic implant, comprising the steps of:

a—dissolving poly(lactic-co-glycolic acid) copolymer (PLGA), containing from 10–100 wt. % lactic acid (LA) units, preferably from 50–90 wt. % LA units, in α-(tetrahydrofuranyl)-ω-hydroxypoly(oxy-1,2-ethandiyl) (glycofurol) to form a liquid;

b—administering said liquid to an animal body; and c—allowing said glycofurol to dissipate to leave a solid implant in said animal body.

The invention also comprises a method of treating an animal, including man, in need of controlled or sustained release of a drug or other biologically active agent, comprising the steps of:

a—dissolving poly(lactic-co-glycolic acid) copolymer (PLGA) containing from 10–100 wt. % lactic acid (LA) units, preferably from 50–90 wt. % LA units, in α-(tetrahydrofuranyl)-ω-hydroxypoly(oxy-1,2-ethandiyl) (glycofurol) to form a liquid;

b—administering a suitable amount of said liquid to an animal in need of such administration; and c—allowing said glycofurol to dissipate in said animal to leave a solid implant composed of a PLGA polymeric matrix;

wherein said liquid further comprises said drug or other biologically active agent, which has been dissolved, dispered or suspended in said glycofurol prior to, concurrently with, or subesquent to said dissolution of PLGA.

The invention also comprises biodegradable implants, whenever prepared by the method of the invention or from a solution of the invention.

As stated, biodegradable implants can serve several functions, including use as a prosthetic or orthodontic implant. The present invention may thus be used where tissue regeneration is desired, e.g. where a growth has been removed from a body and the resulting space requires filling as the tissue grows back, or where ingrowth of bone tissue into a space is necessary. The present invention may also be used for the sustained release of a drug or other biologically active agent. In the context of the invention, a wide variety of drugs and other biological agents, such as peptides (e.g. peptide hormones), proteins (e.g. growth factors, interferons, cytokines and cytokine-binding proteins), oligo- or polynucleotides, and organic compounds (e.g captopril, steroids, prostaglandins and the like), and other molecules with biological function (e.g narcotic antagonists, anti-arrhythmics, anticancer agents, hormone antagonists, contraceptive agents, and anti-inflammatory agents) may be incorporated into the composition; and thus the invention may be employed in the treatment of a variety of diseases or conditions. For example, a controlled-release device containing insulin, prepared from the composition of the invention, can be used in the treatment of diabetes. Other drugs which at present may be delivered by controlled-release systems—such as those systems using microspheres—e.g. leutinizing hormone releasing hormone (LHRH), bromocriptine, or contraceptives, may also be used in context of the present invention.

According to the invention, in those aspects of the invention which require administration to an animal body, the mode of administration of the composition of the invention may be any suitable mode of administration. It will be understood that since one of the advantages of the present invention is the ability to place an implant in an animal body without resorting to surgery, a preferred mode of administration is injection, e.g. through a syringe and needle. It will also therefore be understood that preferred compositions of the invention are those which are injectable, and that preferred methods of the invention are those which employ injection as the means of administration of the compounds of the invention.

EXAMPLES

The foregoing characteristics and advantages of the invention, such as the use of components which have independently been approved for use by the U.S. Food and Drug Administration (FDA) and other national health authorities, will be better understood through the following illustrative and non-limitative examples.

Example 1

Formation and Degradation of Polymeric Composition

Five samples of implants (listed in Table 1) were prepared as follows: Poly(lactic-co-glycolic acid) copolymer (PLGA) (0.6 or 0.8 g) was dissolved in glycofurol (3.4 g or 3.2 g, respectively) at room temperature. A sample of each liquid (4 g) in drops of 250 µl was then poured into water (10 ml phosphate buffered saline solution, PBS, pH 7.4 at 37° C. on shaker bath), and immediately the polymer solidified to form a polymeric composition. The PBS medium was changed daily and the composition surface photographed under a scanning electron microscope at intervals of 4–7 days. As can be seen from FIGS. 1A–1E, which shows the surface of each sample composition from Table 1 at the times after formation indicated, the compositions slowly decay in the aqueous solvent.

TABLE 1

| Sample # | Weight ratio LA/GA units in PLGA | inherent viscosity, dl/g | wt. % PLGA relative to total wt. of sol'n | Appears as Fig. no. |
|---|---|---|---|---|
| 1 | 50/50 | 0.38 | 15 | 1A |
| 2 | 50/50 | 0.38 | 20 | 1B |
| 3 | 50/50 | 0.47 | 15 | 1C |
| 4 | 75/25 | 0.59 | 20 | 1D |
| 5 | 75/25 | 0.59 | 15 | 1E |

Example 2

Figures 1, 1A, 2:
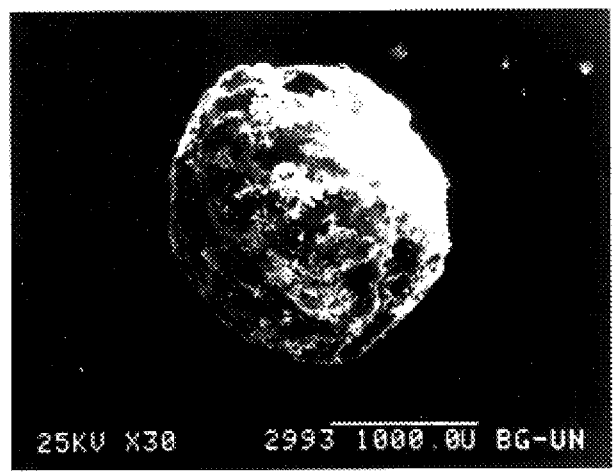
FIG. 2 shows graphically a release profile for the release of bovine serum albumin (BSA) from implants prepared from the solution of the invention as a function of PLGA (1:1 weight ratio LA to GA units, inherent viscosity 0.38 dl/g) concentration in the solution prior to formation of the solid.

Polymeric Composition Containing Protein (BSA) and Effects of Composition on Release Characteristics This example shows that the invention may be used to prepare a controlled-release device, e.g. for medical use, as well as the effects of polymer concentration on the characteristics of release. Three samples as shown in Table 2 were prepared by dissolving PLGA (50/50 LA/GA weight ratio) in glycofurol as in Example 1, but powdered bovine serum albumin (BSA) was dispersed into the PLGA solution using vortex and probe sonication at 50 W for 30 s, while the solution was kept on ice. In vitro release profiles were obtained by injecting 0.25 ml of the solution containing BSA into 10 ml of PBS to obtain solid matrices containing BSA. Samples were continuously shaken at 37° C. Release of BSA was quantitated by measuring the absorbence of the PBS at 280 nm. FIG. 2 shows the release profile of BSA as a function of the PLGA concentration in glycofurol.

TABLE 2

| Sample no. | PLGA, g | Glycofurol, g | BSA, g | shorthand |
|---|---|---|---|---|
| 6 | 0.4 | 3.6 | 0.012 | 10% PLGA 50/50, 3% BSA loading |
| 7 | 0.6 | 3.4 | 0.018 | 15% PLGA 50/50, 3% BSA loading |
| 8 | 0.8 | 3.2 | 0.024 | 20% PLGA 50/50, 3% BSA loading |

Example 3

Effects of Inherent Viscosity on Release Kinetics of BSA

Figures 1, 1A, 2, 3:
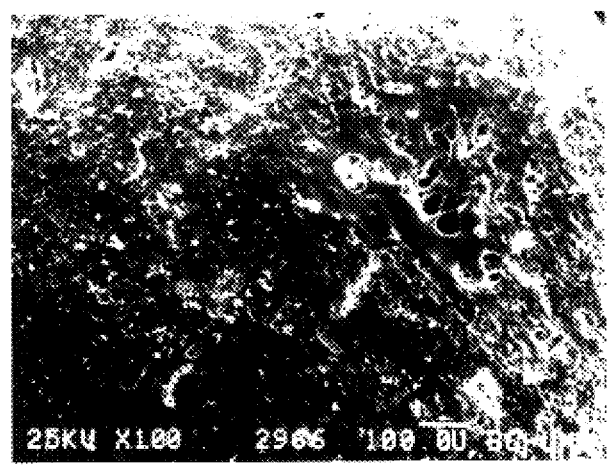
FIG. 3 shows graphically the release profile for the release of BSA from implants prepared from the solution of the invention as a function of inherent viscosity (average molecular weight) of PLGA (1:1 weight ratio LA to GA units)

Two samples analogous to sample 7 were prepared, but using PLGA with inherent viscosity of 0.38 dl/g or 0.47 dl/g. FIG. 3 shows the release kinetics for the matrices so obtained.

Example 4

Effects of BSA Loading on Release Kinetics

Figures 1, 1A, 2, 3, 4:
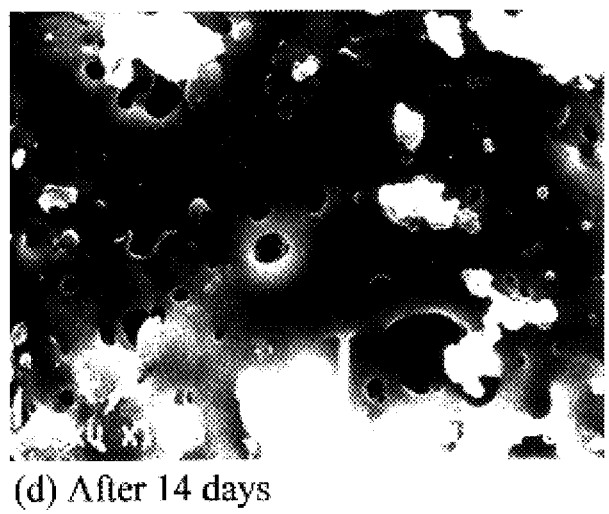
FIG. 4 shows graphically the release profile of BSA from implants prepared from the solution of the invention (PLGA of 1:1 weight ratio LA to GA units, inherent viscosity 0.38 dl/g) as a function of BSA concentration relative to the polymer prior to (and at the time of) formation of the solid.

Samples analogous to sample 7 were prepared using PLGA of inherent viscosity 0.38 dl/g, but the amount of BSA incorporated was varied to be 2, 3, 10, 20 or 30 wt. % relative to the PLGA (2, 3, 10, 20 and 30% loading, respectively) prior to injection. The release profiles of the matrices so obtained can be seen in FIG. 4.

Example 5

Effects of Ratio of LA/GA Unit Ratio on Release Kinetics

Figures 1, 1A, 2, 3, 4, 5:
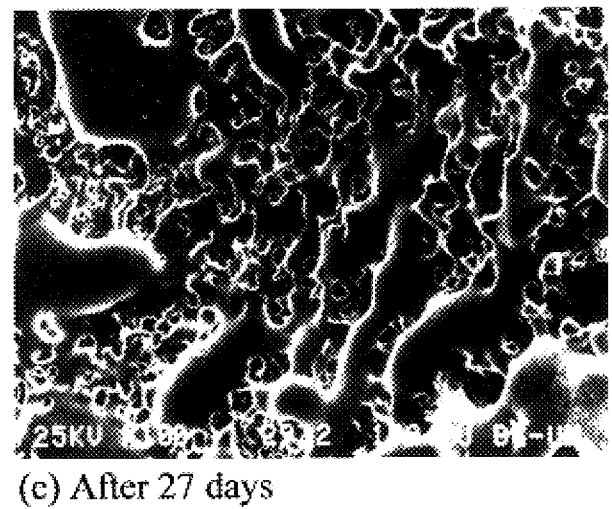
FIG. 5 shows graphically the release profile of BSA from implants prepared from the solution of the invention (PLGA of 3:1 weight ratio LA to GA units, inherent viscosity 0.59 dl/g) as a function of BSA concentration relative to the polymer prior to (and at the time of) formation of the solid.

Samples analogous to sample 6 were prepared using PLGA containing an LA/GA weight ratio of 3:1 (inherent viscosity 0.59 dl/g), with BSA loading varied to be 1.5, 3, 10, 20 or 30%. The release profiles of the matrices so obtained can be seen in FIG. 5.

Example 6

Effects of Inherent Viscosity on Release Kinetics of sp55-R

Figures 1, 1A, 2, 3, 4, 5, 6:
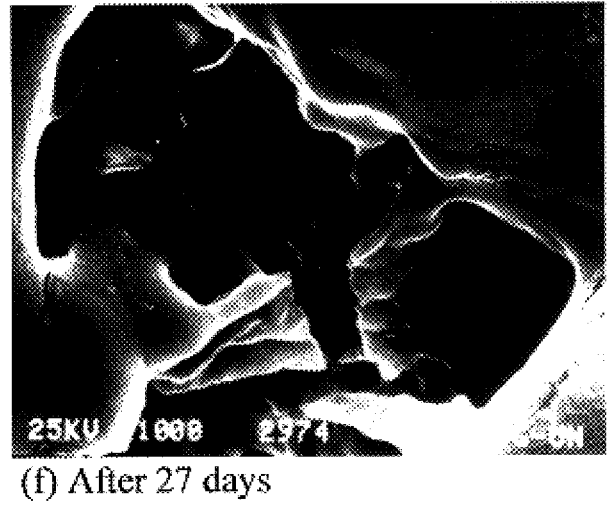
FIG. 6 shows graphically the release profile of human soluble p55 tumor necrosis factor receptor (sp55-R) from implants prepared from the formulation of the invention as a function of inherent viscosity (average molecular weight) of PLGA (1:1 weight ratio LA to GA units)
Figures 1, 1B:
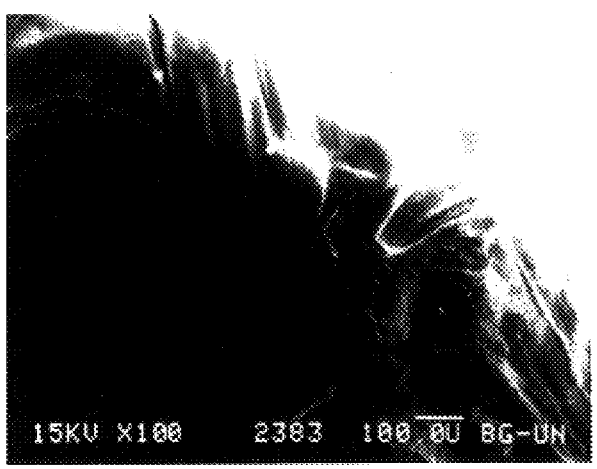
Figures 1, 1B, 2:
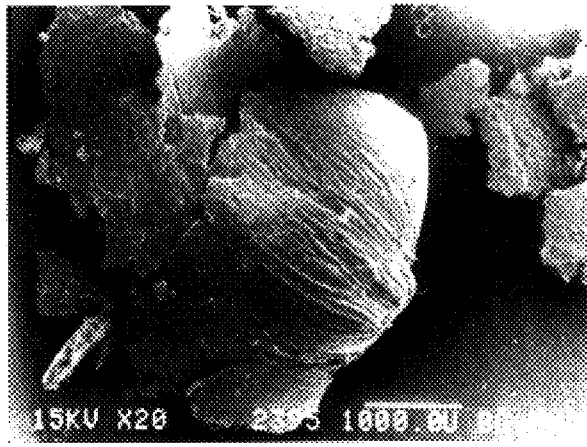
Figures 1, 1B, 2, 3:
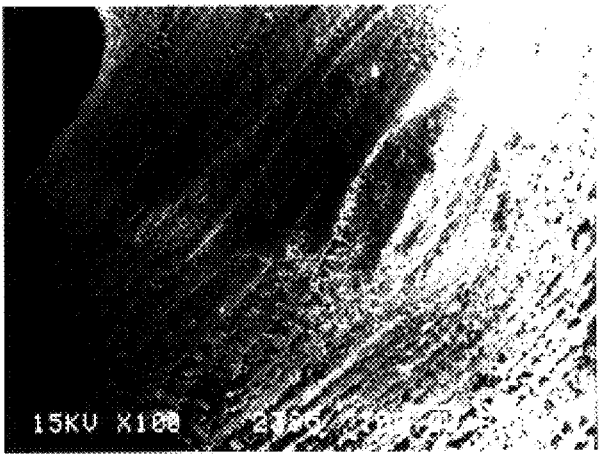
Figures 1, 1B, 2, 3, 4:
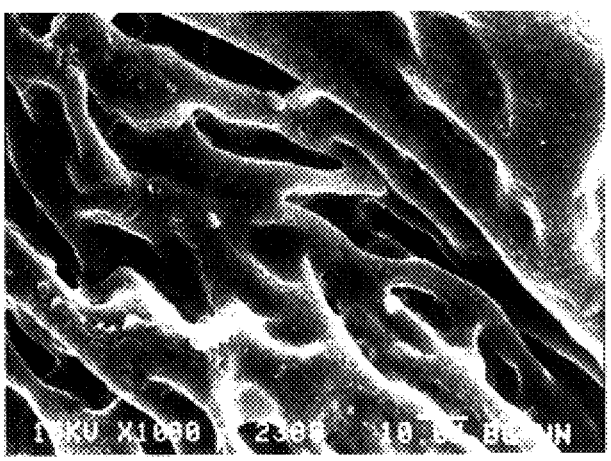
Figures 1, 1B, 2, 3, 4, 5:
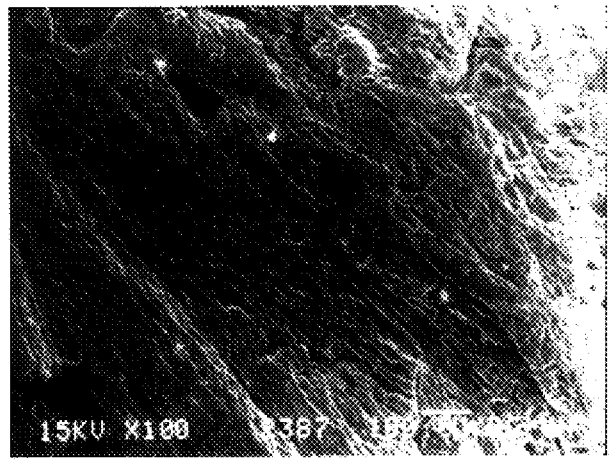
Figures 1, 1B, 2, 3, 4, 5, 6:
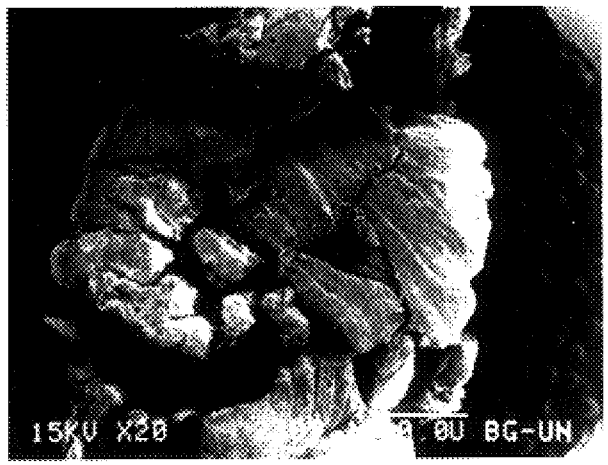
Figures 1, 1C:
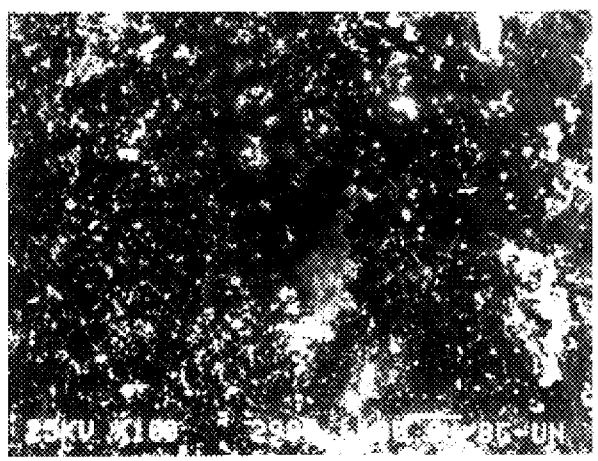
Figures 1, 1C, 2:
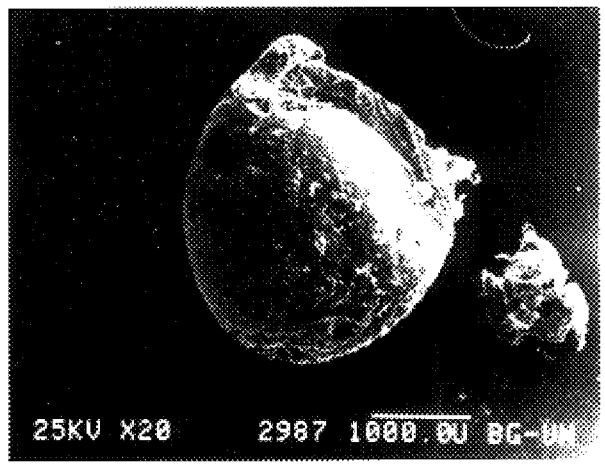
Figures 1, 1C, 2, 3:
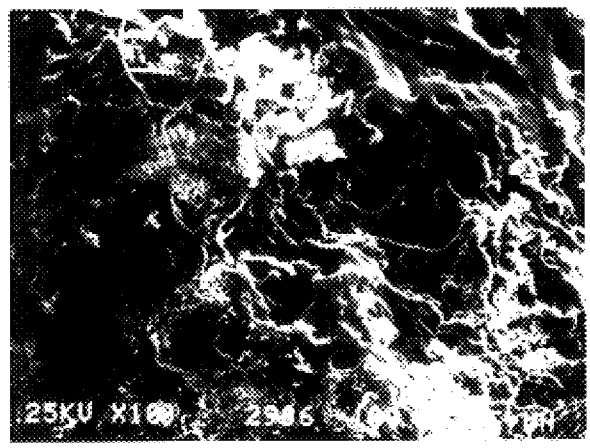
Figures 1, 1C, 2, 3, 4:
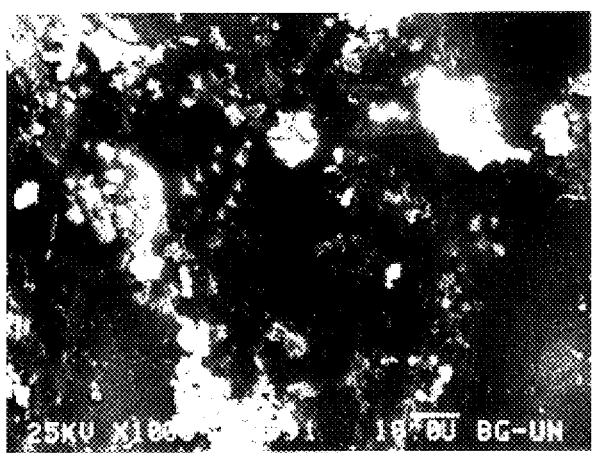
Figures 1, 1C, 2, 3, 4, 5:
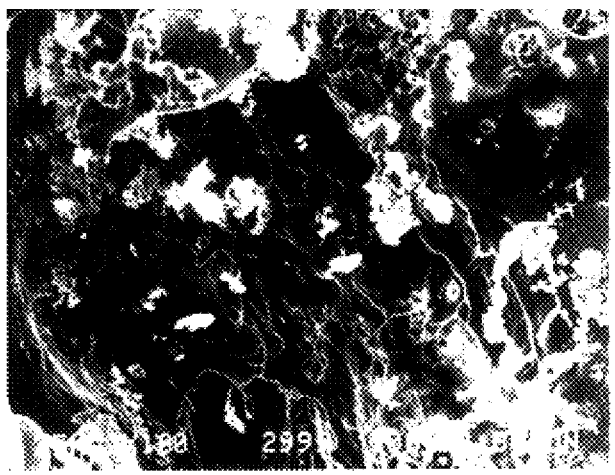
Figures 1, 1C, 2, 3, 4, 5, 6:
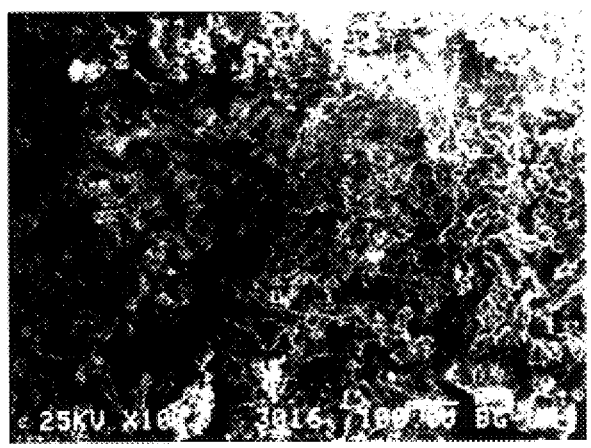
Figures 1, 1D:
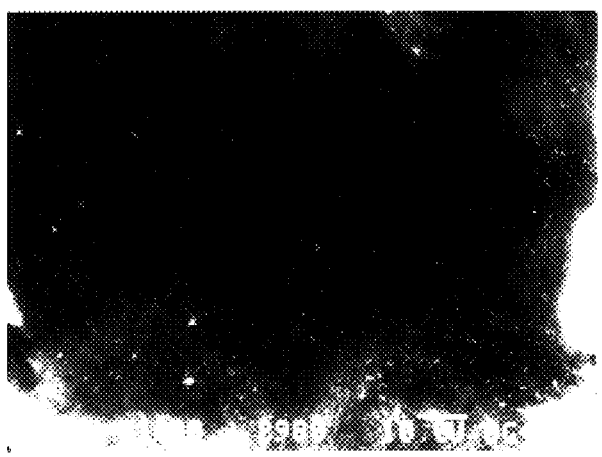
Figures 1, 1D, 2:
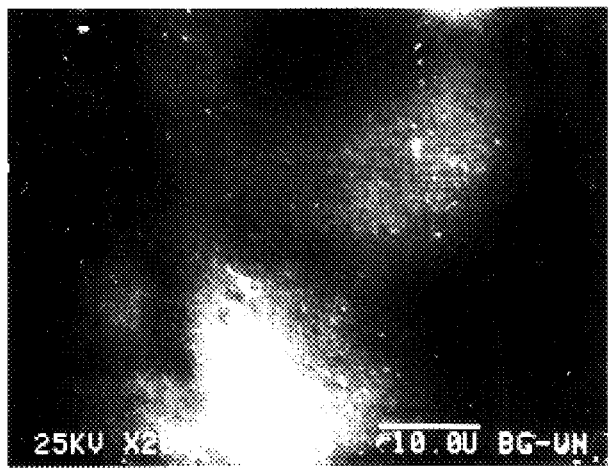
Figures 1, 1D, 2, 3:
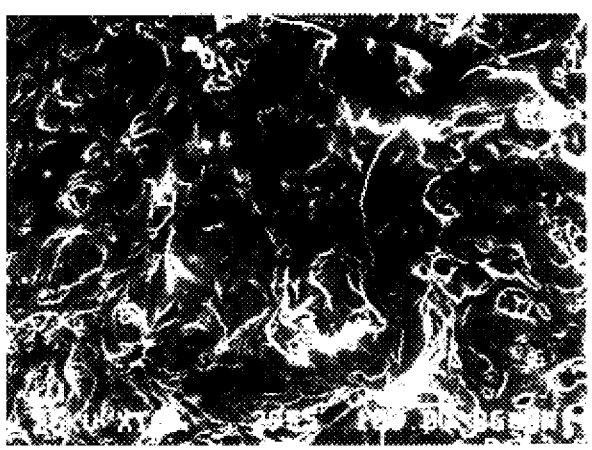
Figures 1, 1D, 2, 3, 4:
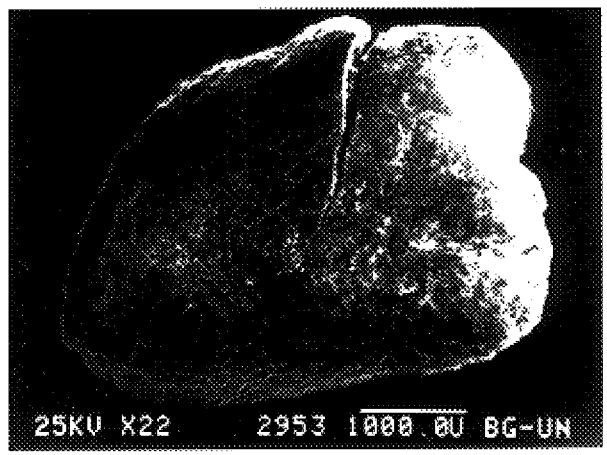
Figures 1, 1D, 2, 3, 4, 5:
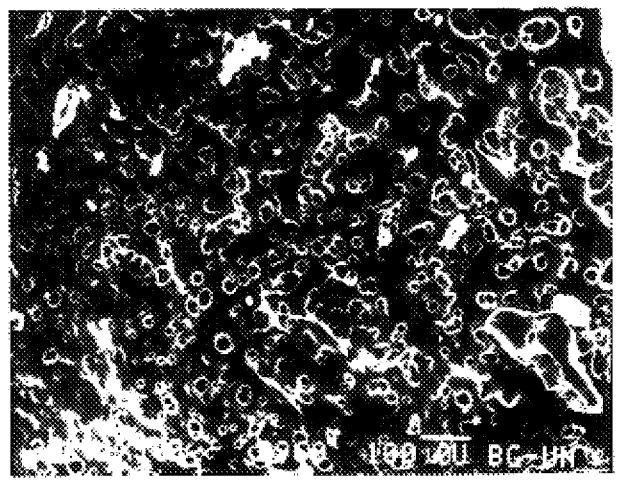
Figures 1, 1D, 2, 3, 4, 5, 6:
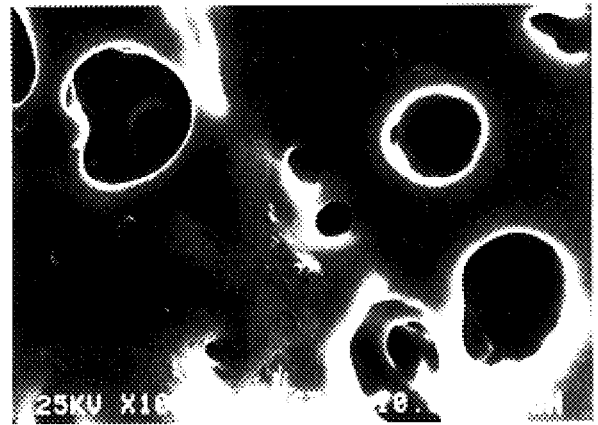
Figures 1, 1E:
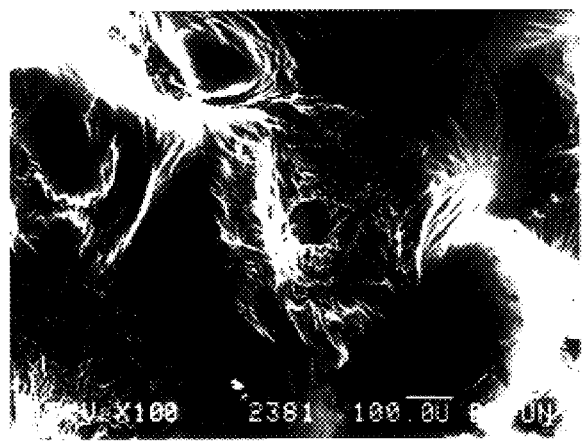
Figures 1, 1E, 2:
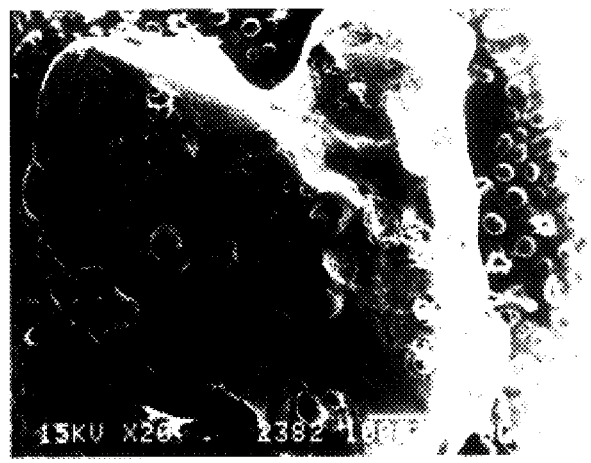
Figures 1, 1E, 2, 3:
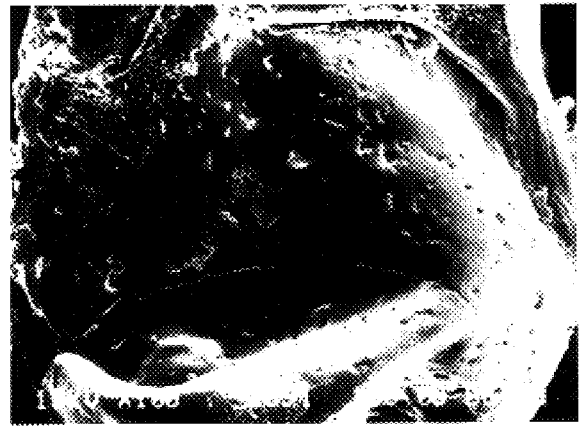
Figures 1, 1E, 2, 3, 4:
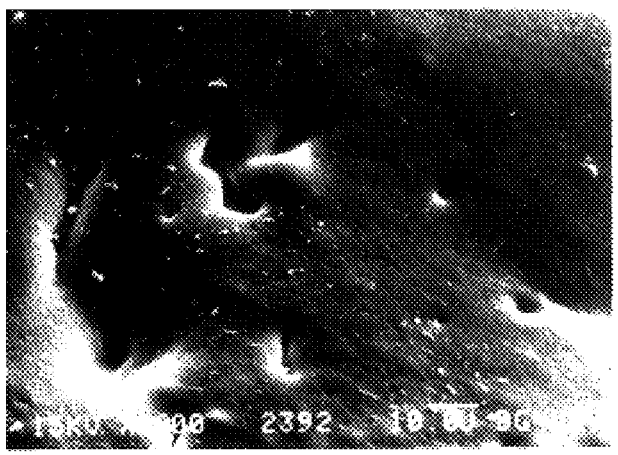
Figures 1, 1E, 2, 3, 4, 5:
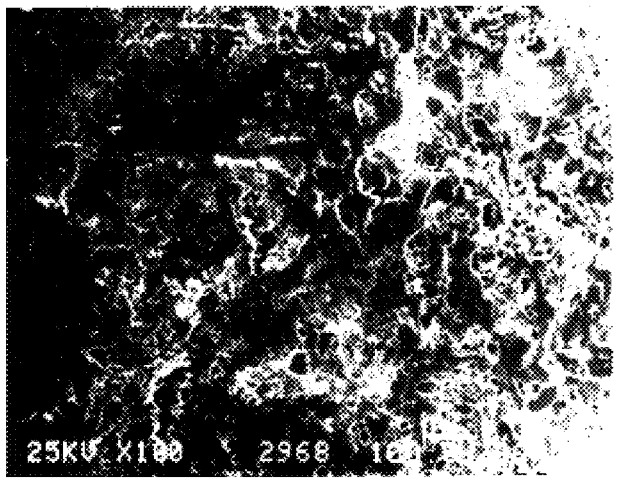
Figures 1, 1E, 2, 3, 4, 5, 6:
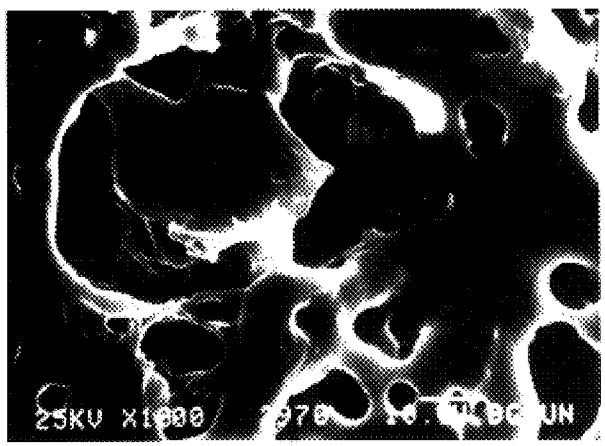
Figure 2:
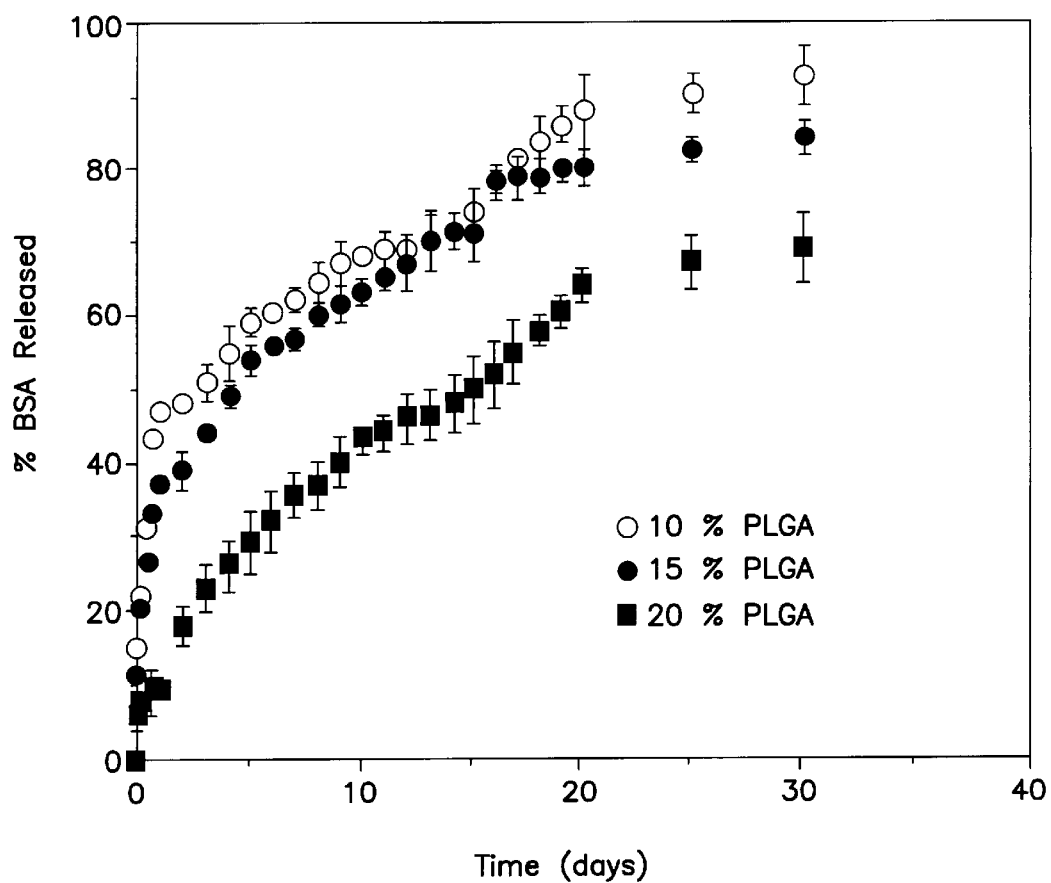
Figure 3:
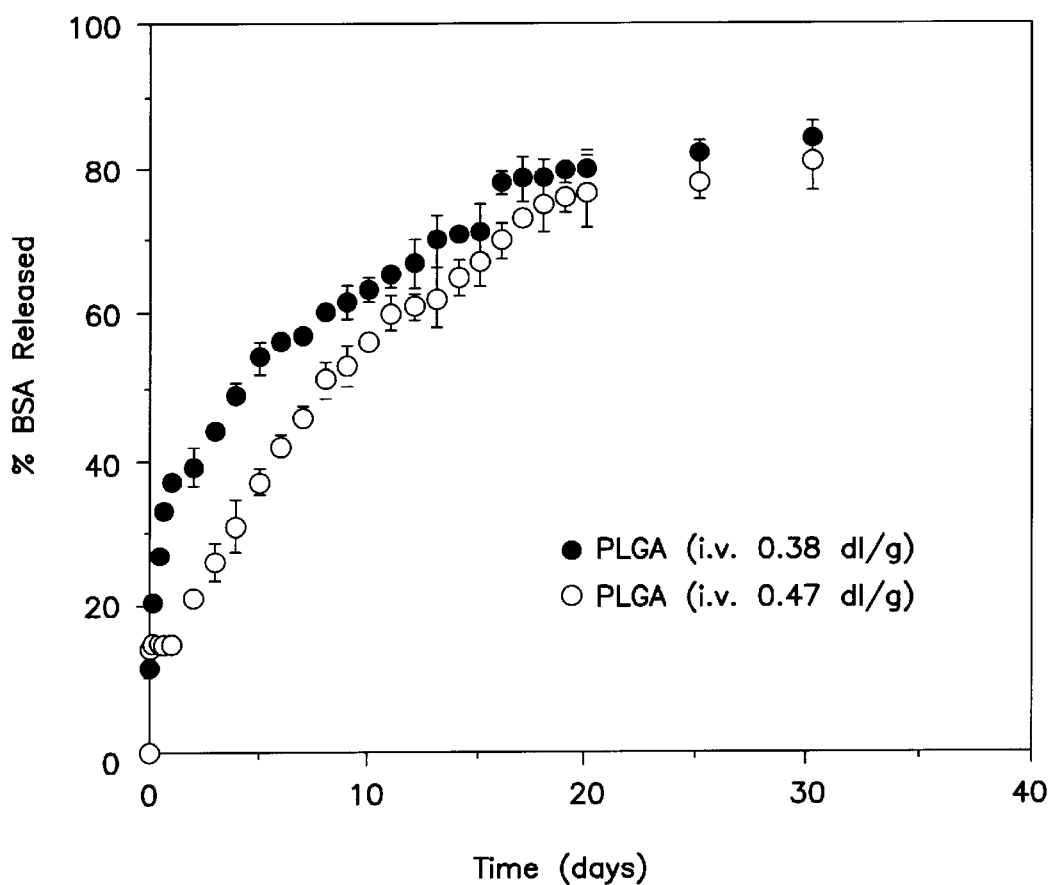
Figure 4:
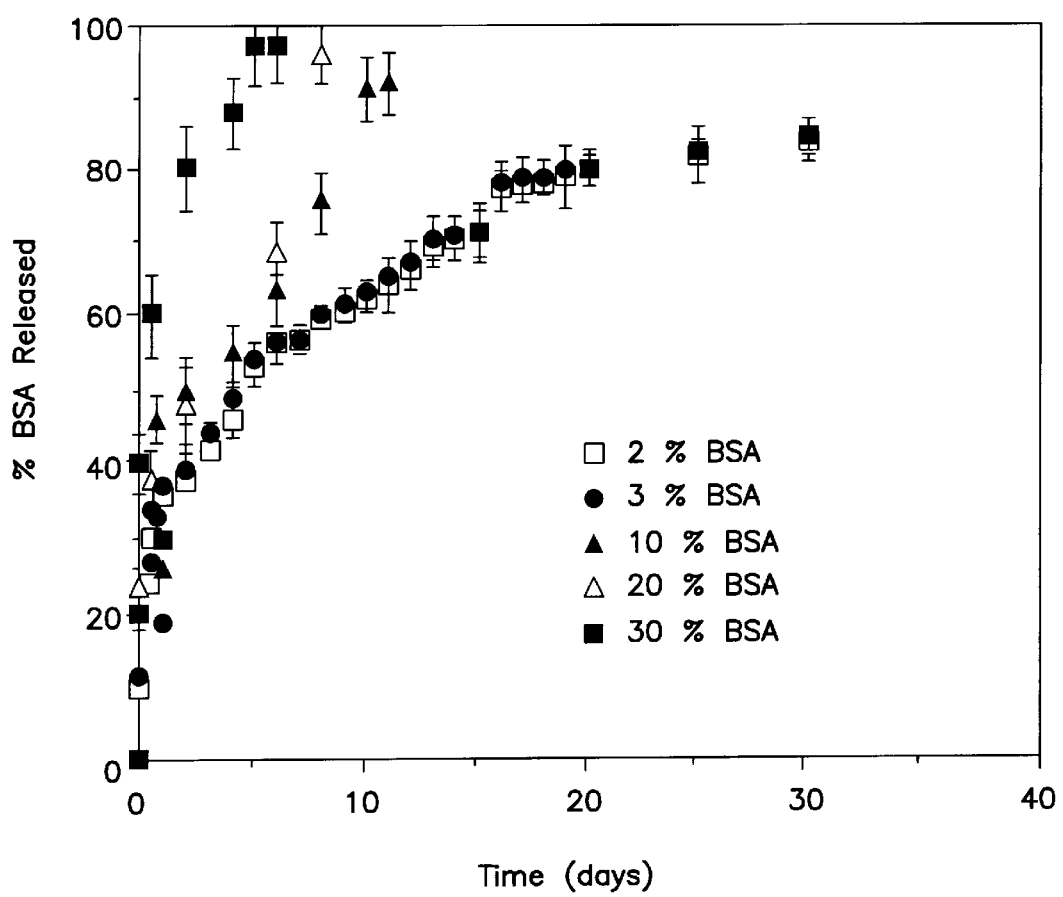
Figure 5:
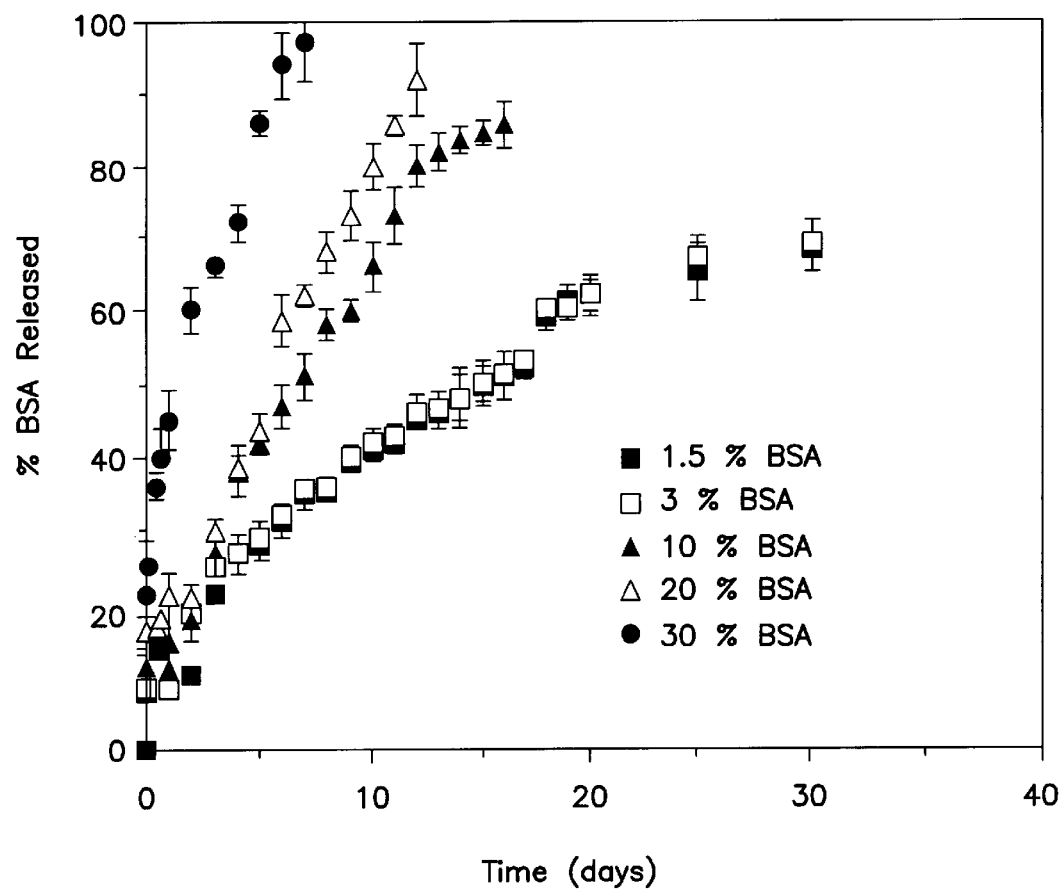
Figure 6:
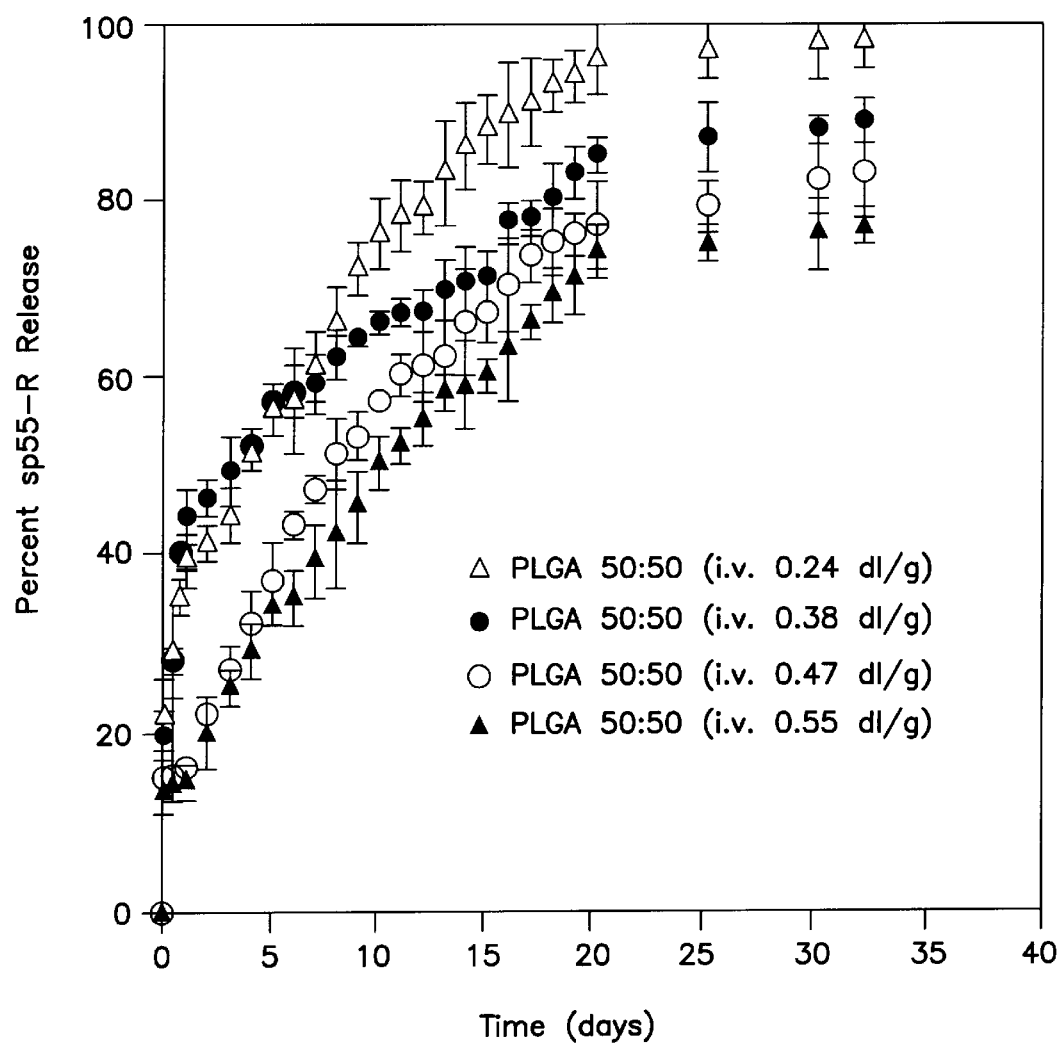

Four samples analogous to sample 6 were prepared, using PLGA (1:1 LA/GA weight ratio) with inherent viscosity of 0.24 dl/g, 0.38 dl/g, 0.47 dl/g and 0.55 dl/g, and using a powder mixture of sp55-R and BSA (3 wt. % total protein relative to polymer) in a 1:20 weight ratio. FIG. 6 shows the release kinetics for the matrices so obtained.

Example 7

Figure 7:
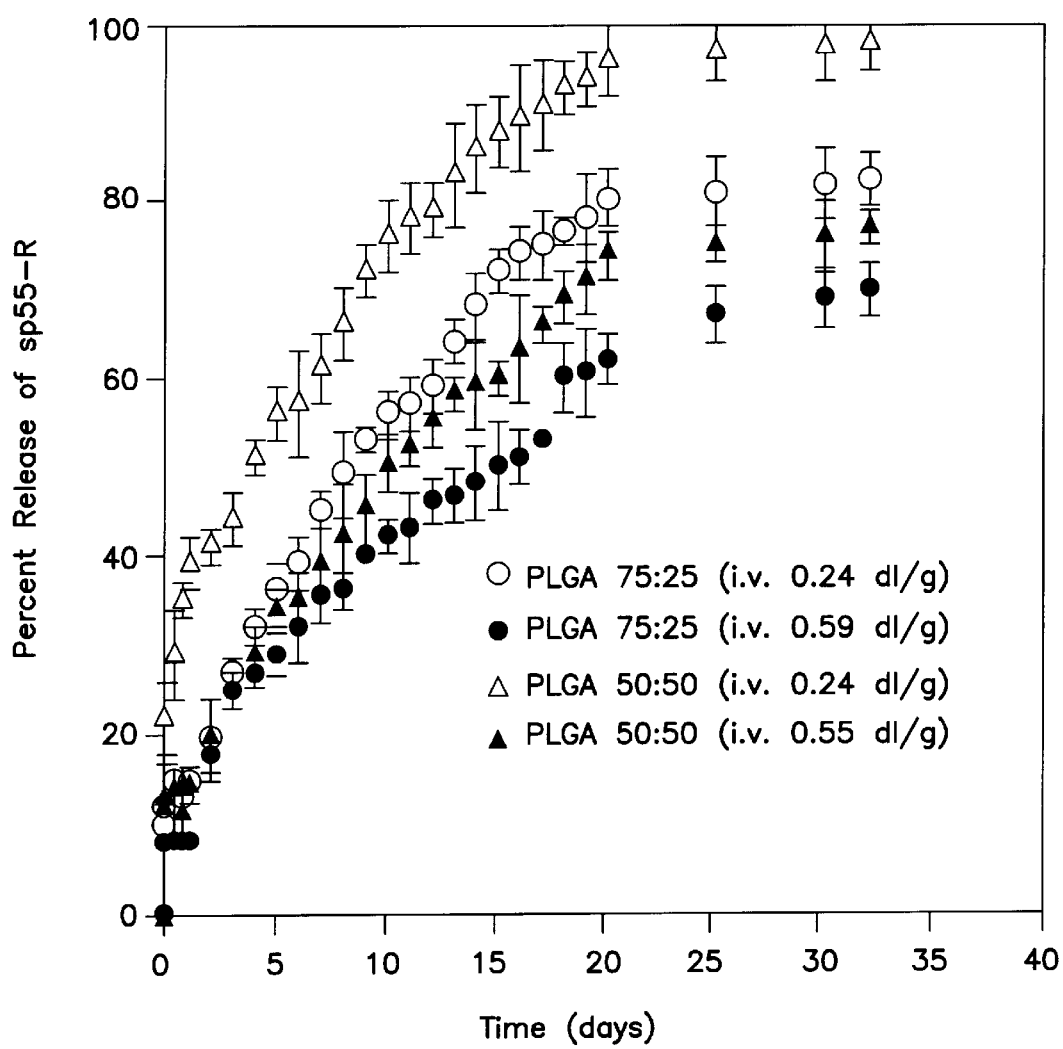
FIG. 7 shows graphically the release profile of sp55-R from implants prepared from the solution of the invention as a function of inherent viscosity (average molecular weight) of PLGA (3:1 weight ratio LA to GA units)

Effects of Inherent Viscosity and Ratio of LA/GA Unit Ratio on Release Kinetics of sp55-R Four samples analogous to sample 6 were prepared, using PLGA (1:1 or 3:1 LA/GA weight ratio) with inherent viscosity of 0.24 dl/g or 0.55 dl/g, and using a powder mixture of sp55-R and BSA (3 wt. % total protein relative to polymer) in a 1:20 weight ratio. FIG. 7 shows the release kinetics for the matrices so obtained.

Example 8

Release Kinetics of Mixtures of BSA and sp55-R

Figure 8:
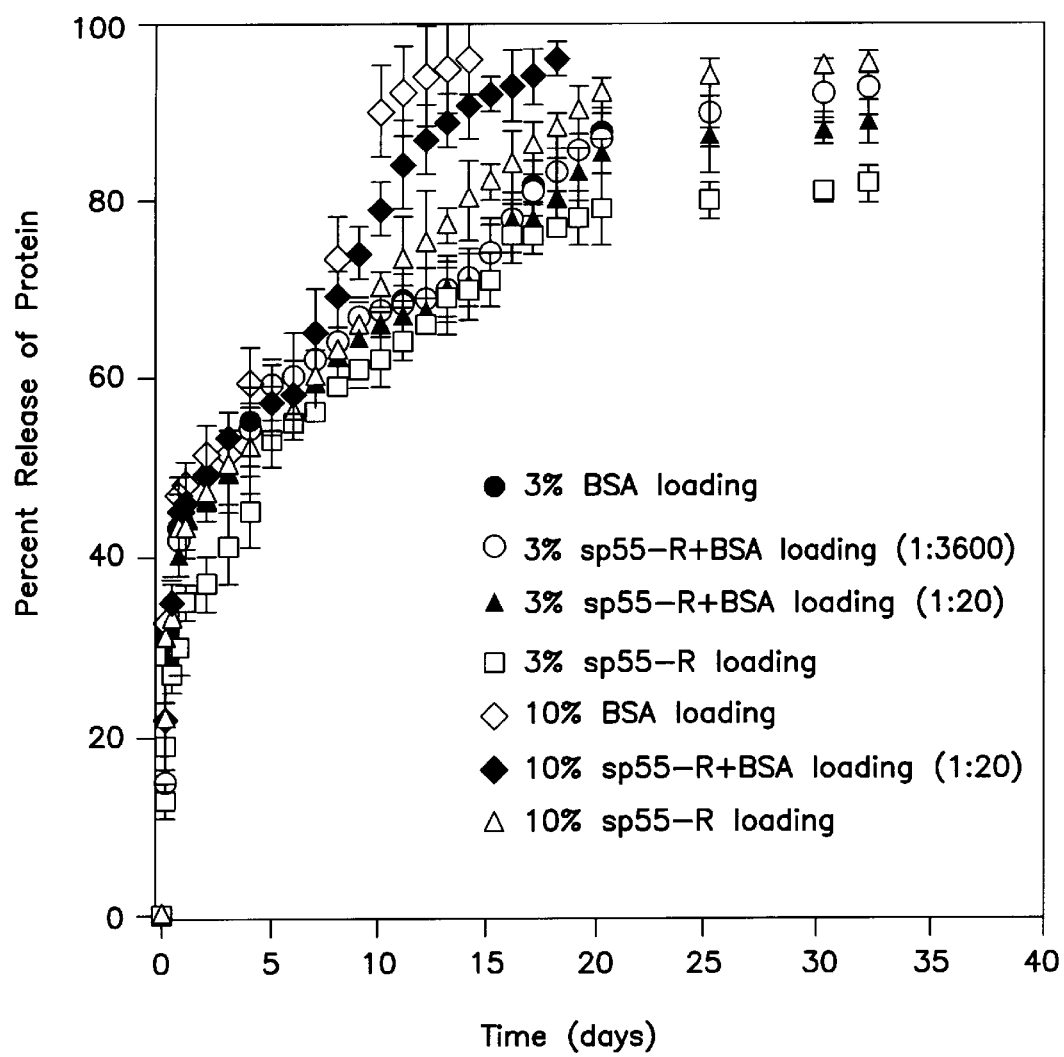
FIG. 8 shows graphically the release profile of the total amount of protein (BSA alone, sp55-R alonge, or BSA together with sp55-R) from implants prepared from the solution of the invention (PLGA with 1:1 weight ratio LA to GA units) as a function of the ratio of sp55-R to BSA (1:20 or 1:3600) and as a function of total protein loading (3 wt. % or 10 wt. % relative to the weight of the polymer)

Samples analogous to sample 6, containing either BSA alone, sp55-R alone, or a combination of BSA and sp55-R in a weight ratio of 20:1 or 3600:1, and loaded with 3 wt. % or 10 wt. % total protein relative to the weight of the polymer (PLGA with a 1:1 weight ratio of LA/GA), were prepared. FIG. 8 shows the release kinetics of protein from these matrices.

Example 9

Release Kinetics of Mixtures of BSA and sp55-R

Figure 9:
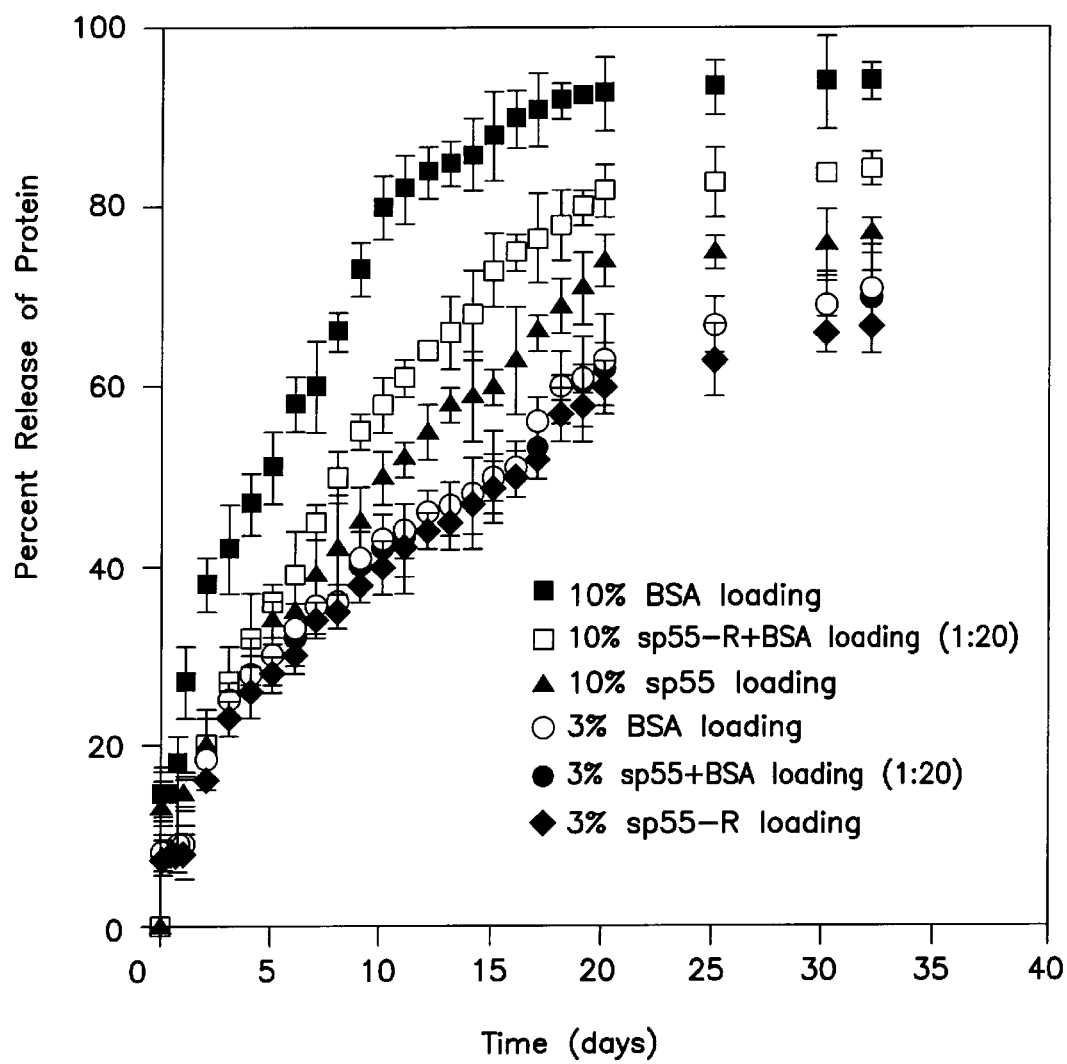
FIG. 9 shows graphically the release profile of the total amount of protein (BSA alone, sp55-R alone, or BSA together with sp55-R) from implants prepared from the solution of the invention (PLGA with 3:1 weight ratio LA to GA units) as a function of the ratio of sp55-R to BSA (1:20 or 1:3600) and as a function of total protein loading (3 wt. % or 10 wt. % relative to the weight of the polymer)

Samples analogous to sample 6, containing either BSA alone, sp55-R alone, or a combination of BSA and sp55-R in a weight ratio of 20:1, and loaded with 3 wt. % or 10 wt. % total protein relative to the weight of the polymer (PLGA with a 3:1 weight ratio of LA/GA), were prepared. FIG. 9 shows the release kinetics of protein from these matrices.

Example 10

Release of sp55-R From Compositions in Mice and Protection of Mice From Chronic Exposure to Tumor Necrosis Factor (TNF)

Balb/c and Balb/c nude female mice, aged 8–9 weeks and weighing 20–21 g each, were injected with formulations of the invention containing sp55-R alone or in combination with BSA (or with formulations devoid of protein), and the release kinetics of sp55-R (and BSA) from the implant which resulted were measured; when the formulations contained sp55-R, the receptor was present in an amount of about 7–20 $\mu$g per mouse. As shown in the FIGS. 10–14, the formulations used contained 10 wt. % (and in FIGS. 11 and 13, 20 wt. % as well) PLGA (with a 1:1 weight ratio LA/GA units in FIGS. 10 and 11, and a 3:1 LA/GA weight ratio in FIGS. 12 and 13) in glycofurol, 3 wt. % to 10 wt. % total protein loading vs. polymer when containing protein, and BSA and sp55-R in a weight ratio of 20:1 when a mixture of BSA and sp55-R was used.

Figure 10A:
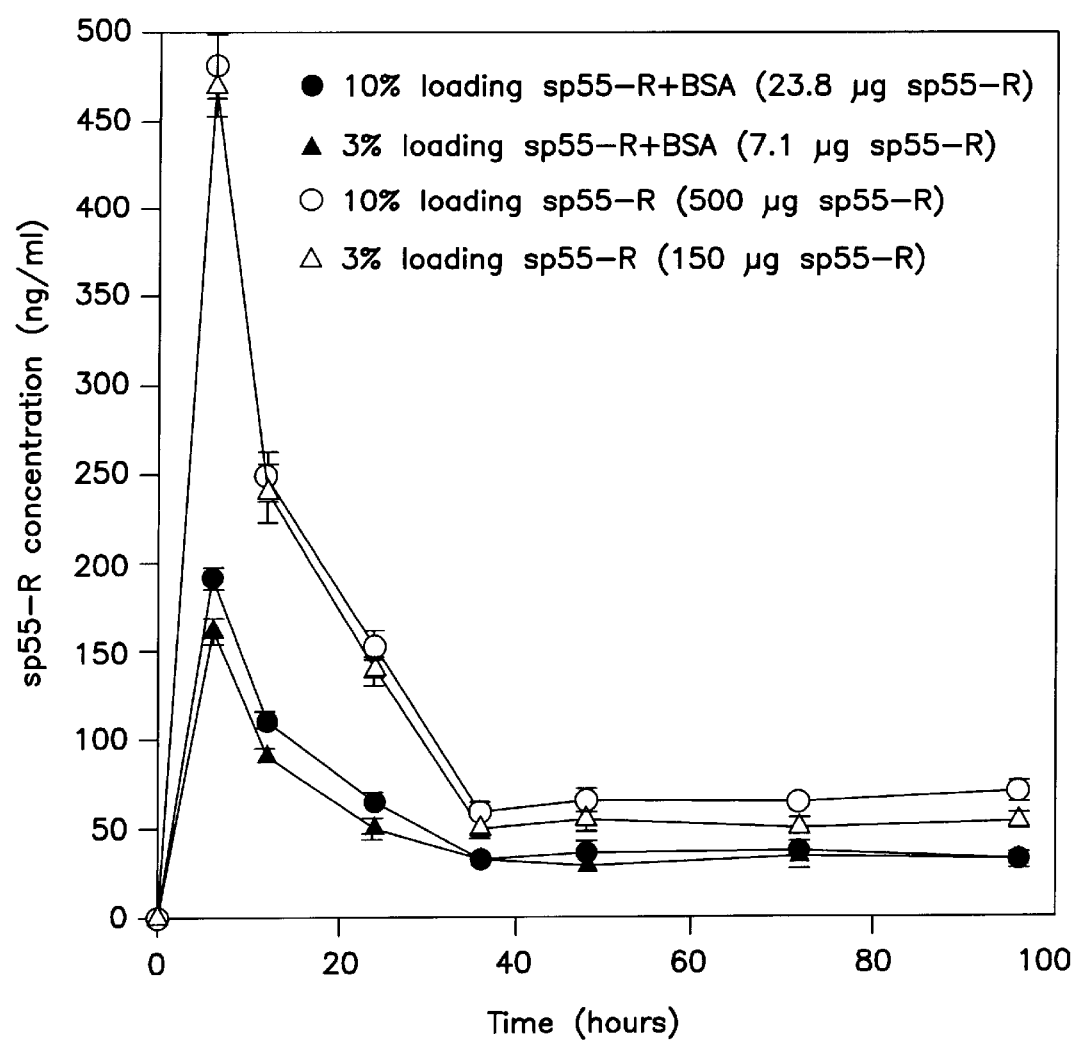
FIG. 10A shows the effect of the amount of protein loaded (3 wt. % and 10 wt. % with reference to polymer) and the nature of the protein (sp55-R alone or with BSA in a 1:20 weight ratio) on the release rate of protein from a 0.05 g formulation of 10 wt. % PLGA in glycofurol (1:1 weight ratio LA/GA units, 0.38 dl/g inherent viscosity) over a period of 100 hours.
Figure 10B:
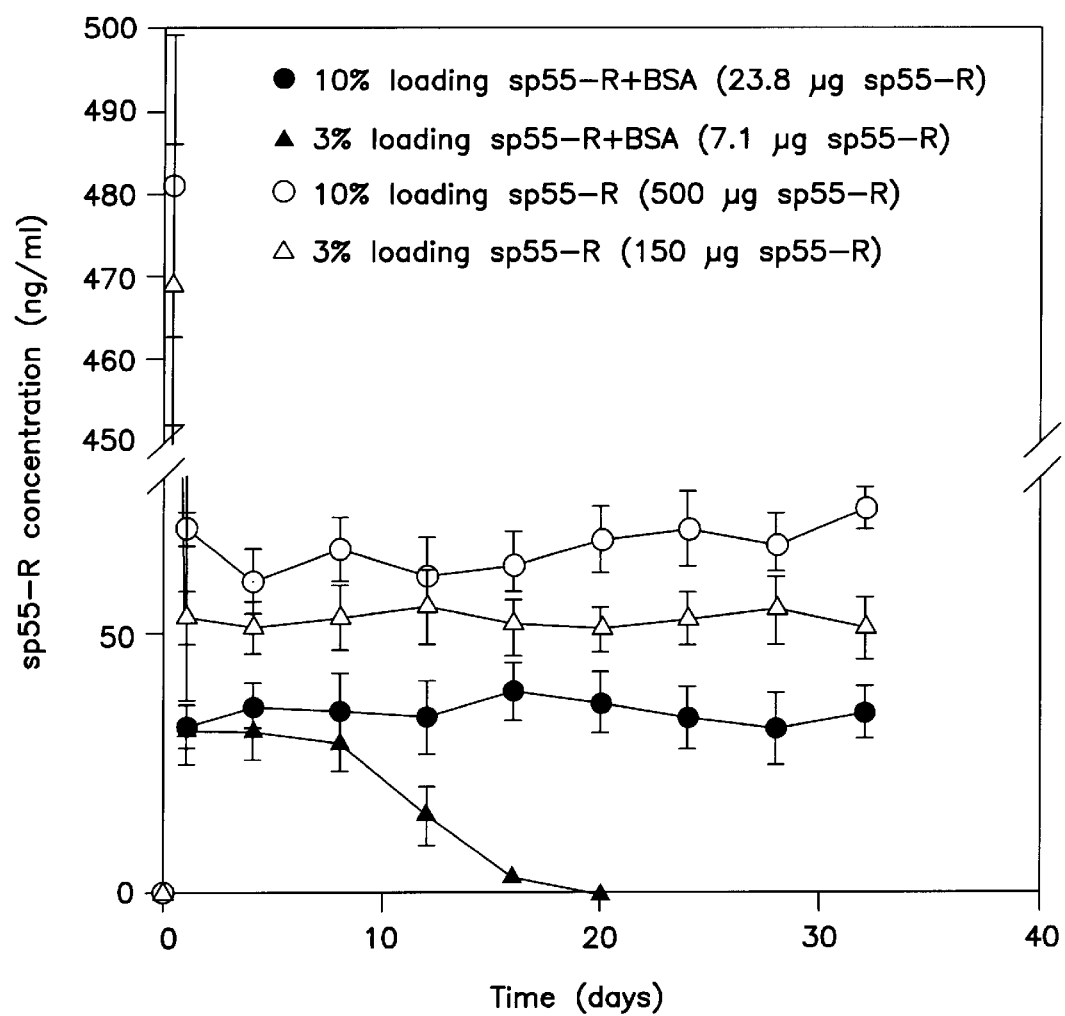
FIG. 10B shows the same profile over a period of 35 days.
Figure 11:
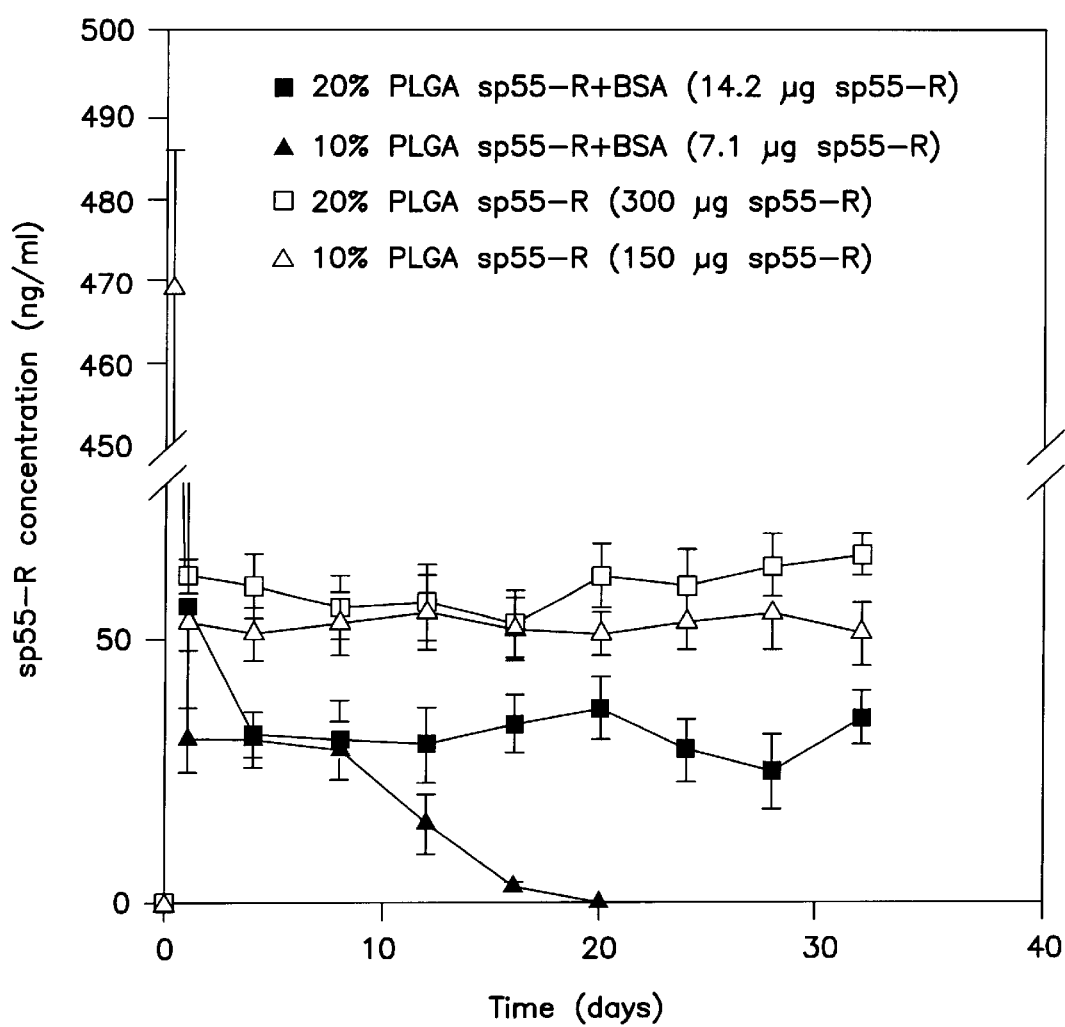
FIG. 11 shows the effect of polymer concentration (10 wt. % and 20 wt. % with reference to glycofurol, 1:1 weight ratio LA/GA units, inherent viscosity of 0.38 dl/g, 3 wt. % total protein relative to polymer) and the nature of the protein on the release rate over a period of over 30 days.
Figure 12A:
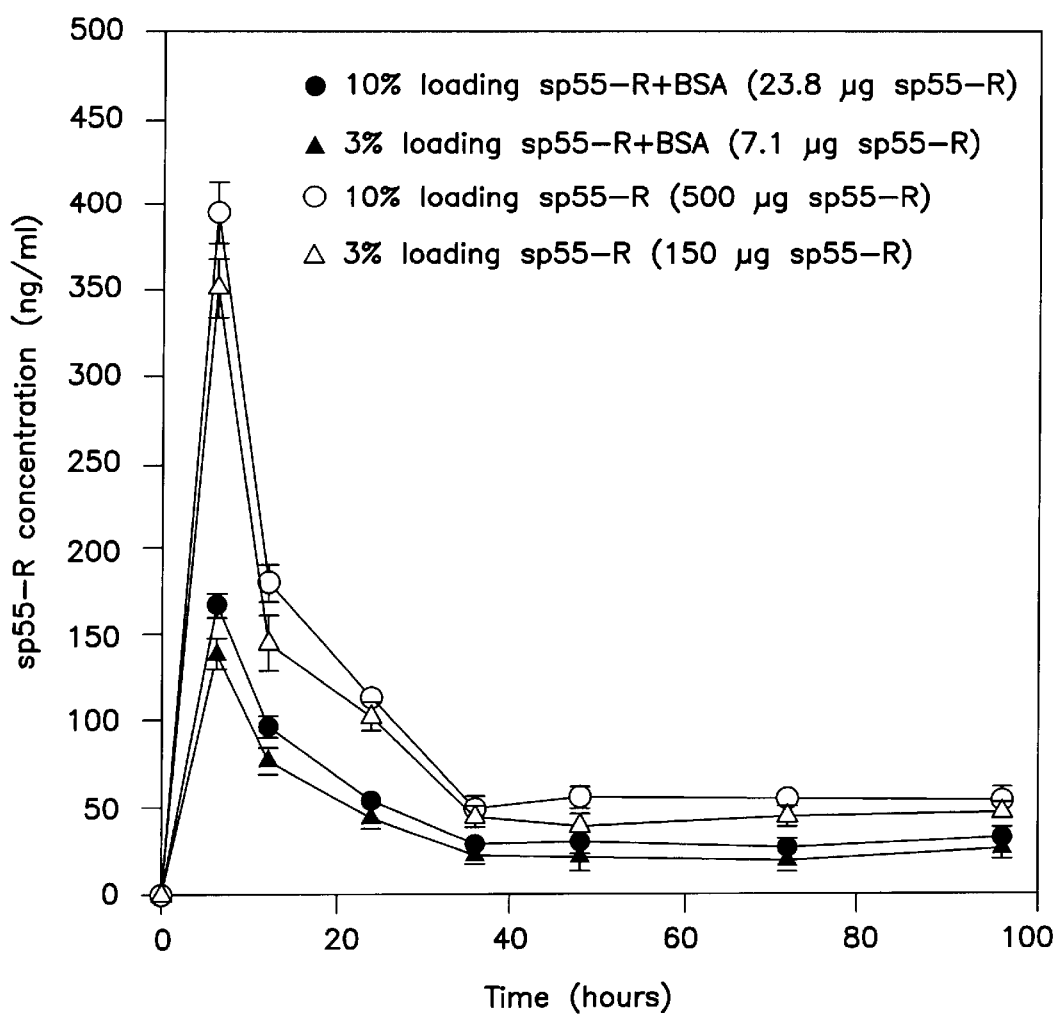
FIGS. 12A and 12B are similar to FIGS. 10A and 10B, respectively, but for polymer with a 3:1 ratio LA/GA units, 0.59 dl/g inherent viscosity.
Figure 12B:
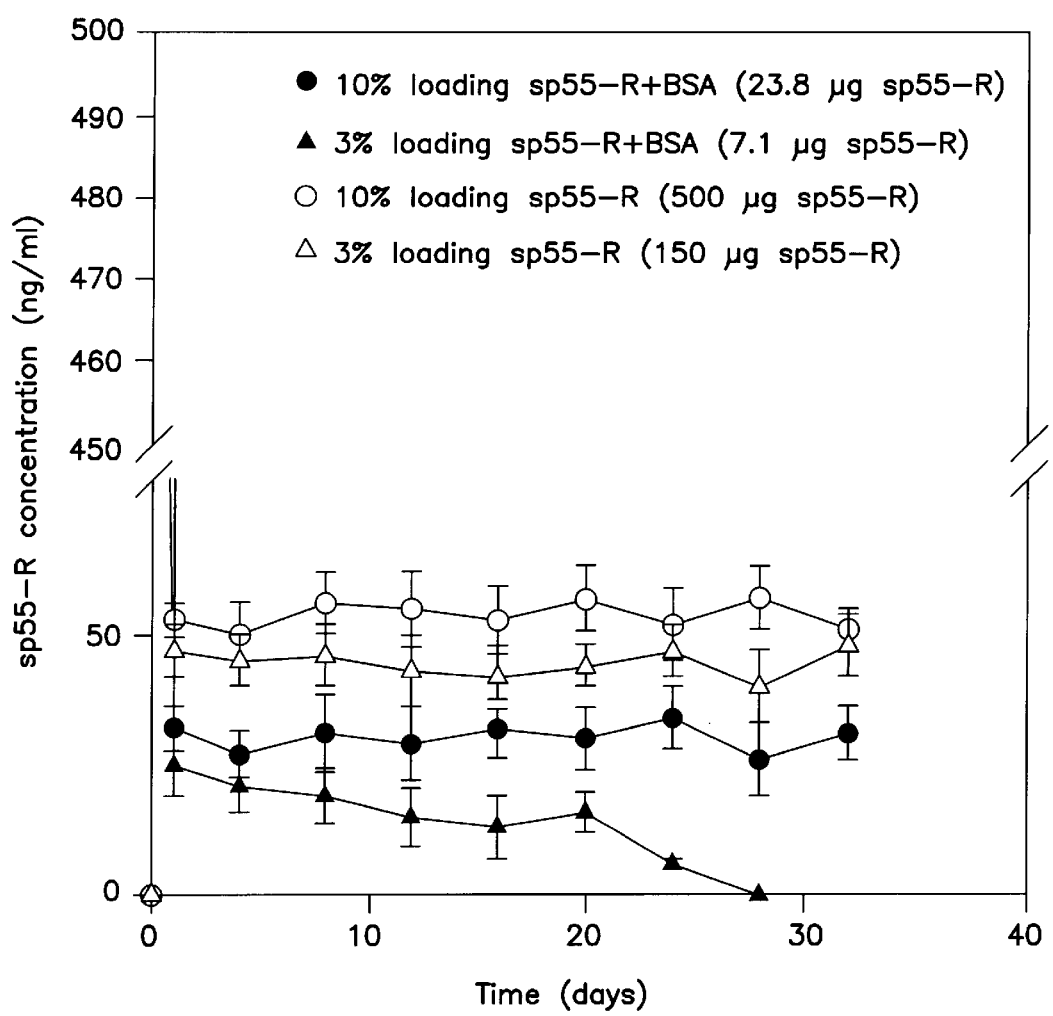
Figure 13:
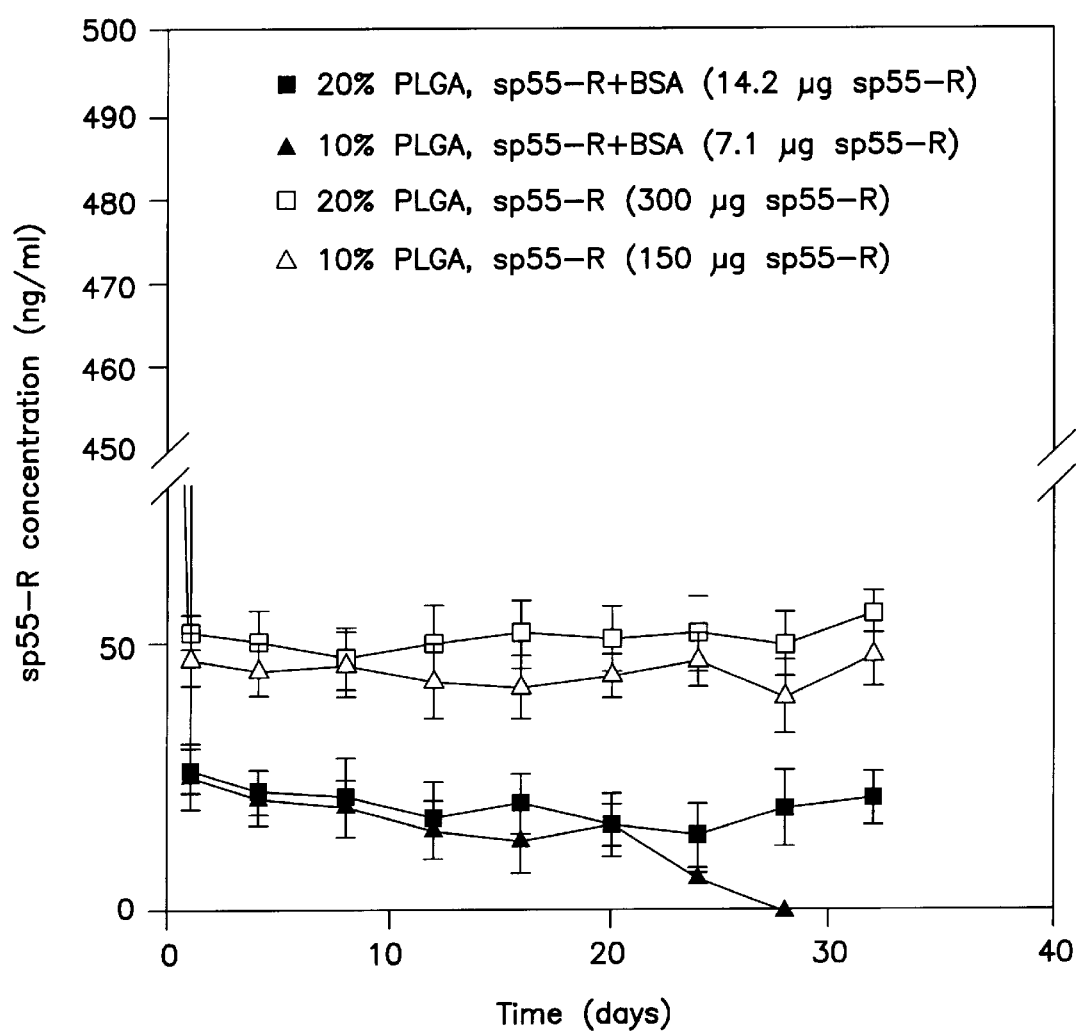
FIG. 13 is similar to FIG. 11, but for polymer with a 3:1 ratio LA/GA units, 0.59 dl/g inherent viscosity.

Serum samples were collected periodically after injections by tail bleeding and via the eye artery, and allowed to clot. The sp55-R level in these serum samples was determined by a 2-site capture enzyme-linked immunosorbent assay (ELISA). FIGS. 10A and 12A show that after about 36 hours, the rate of release of protein remained stable for the next several days, and FIGS. 10B, 11, 12B and 13 show that this rate of release remained stable over a period of several weeks. FIGS. 11 and 13 show that the concentration of polymer used (10 wt. % vs. 20 wt. %) had negligible effect on the release profile.

Some of the mice used to determine the protein release profiles were also used to determine the effectiveness of the formulation of the invention as a means for mitigating the effects of chronic exposure to TNF. Balb/c nude female mice, aged 8–9 weeks and weighing 20–21 grams, were inoculated subcutaneously in the flank area with Chinese hamster ovary (CHO) cells transfected with the TNF gene and expressing TNF. Injection of the PLGA formulation into these mice was performed 5 days after tumor cell inoculation.

It is known that nude mice bearing TNF-producing tumors exhibit severe cachexia, leading to death (Oliff et al., Cell 50:555–563 (1987)). Injection of TNF-binding proteins, such as TNF-binding antibodies or TNF receptors, can temporarily mitigate these effects, but the injected proteins are rapidly cleared from the body, making direct injection of TNF-binding compounds a less-than-ideal means for mitigating the effects of chronic TNF exposure.

Figure 14:
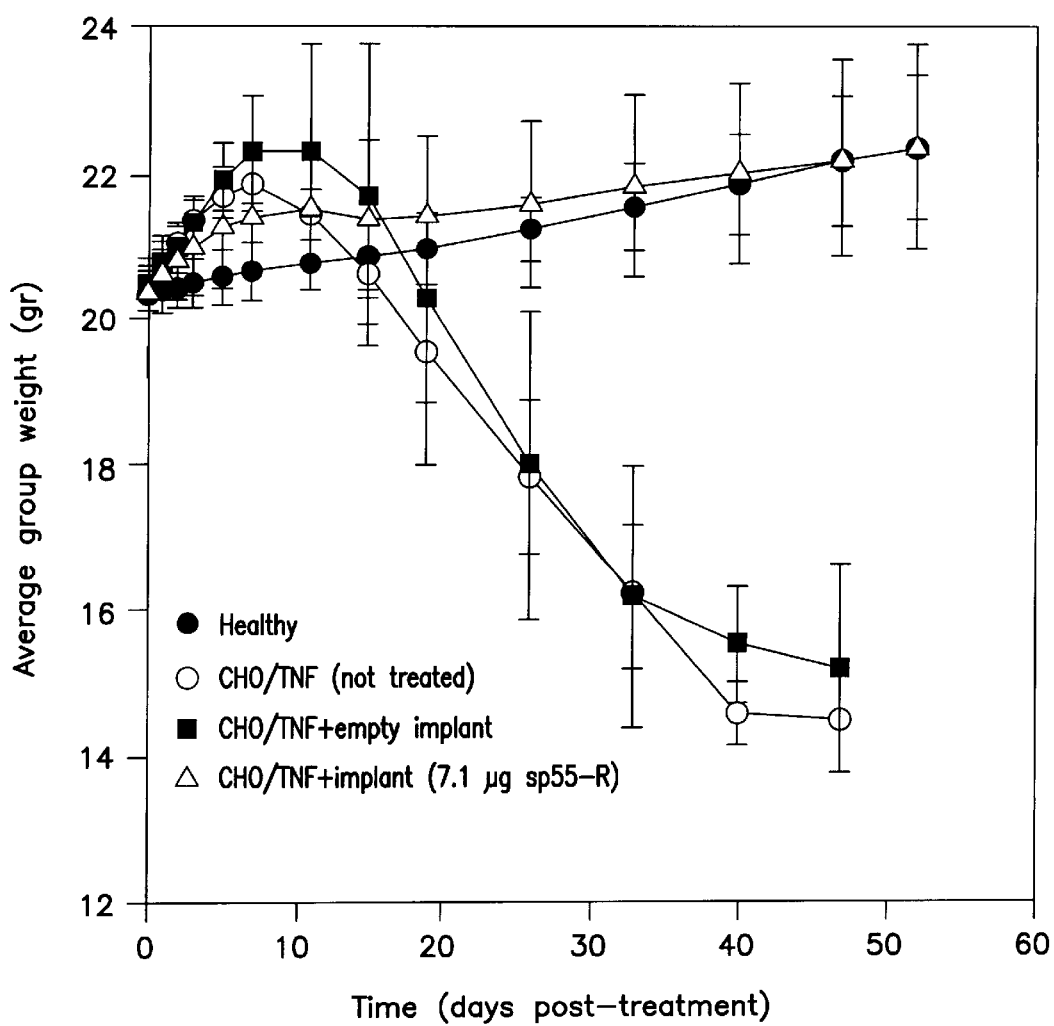
FIG. 14 shows the effect of injection of formulas of the invention on the weights of tumor-bearing mice.
Figure 16:
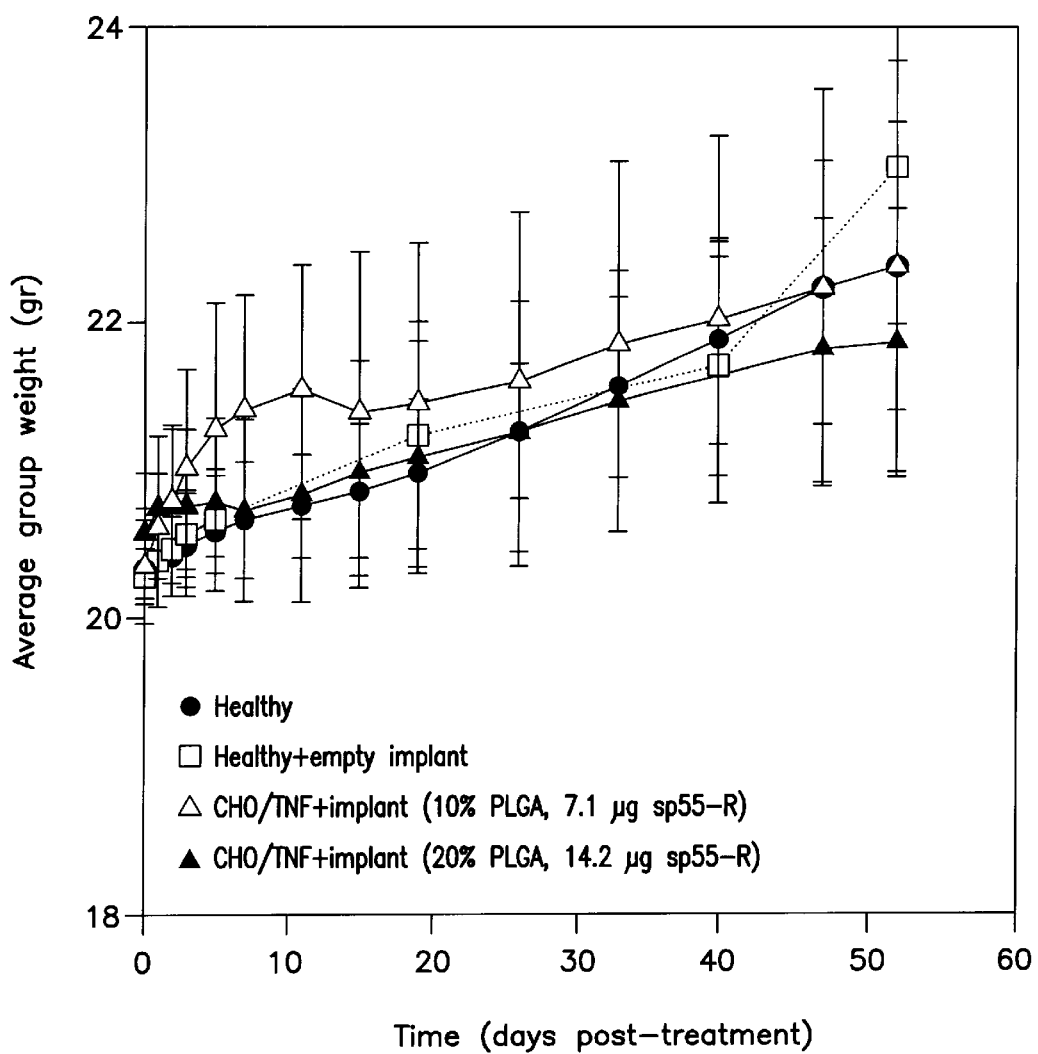
FIG. 16 shows the rate of weight gain of tumor-bearing mice treated with compositions of the invention in comparison to the weight gain of healthy mice.

In accordance with the invention, however, injection of PLGA formulations containing sp55-R into such tumor-bearing mice (about 7 to 20 $\mu$g receptor/mouse) prevented body weight loss (body weight increased naturally). This is illustrated in FIG. 14, which shows that over a period of 50 days, the weight of tumor-bearing mice treated with a formulation of the invention (10 wt. % PLGA (3:1 LA:GA ratio), 0.59 dl/g in glycofurol, 3 wt. % loading of sp55-R with BSA (7.1 $\mu$g sp55-R)) ($\Delta$) increased at a similiar rate to that of healthy Balb/c nude mice (●); whereas untreated tumor-bearing mice (○) and tumor-bearing mice injected with a formulation of the invention containing only polymer (■) lost about 25% body weight over the course of the experiment. In FIG. 16, it can be seen that tumor-bearing mice mice injected with TNF-loaded implants containing 20 wt. % polymer relative to glycofurol (▲) gained weight at a rate comparable to the rate of weight gain of tumor-bearing mice injected with TNF-loaded formulation containing 10 wt. % polymer relative to glycofurol ($\Delta$).

Figure 15:
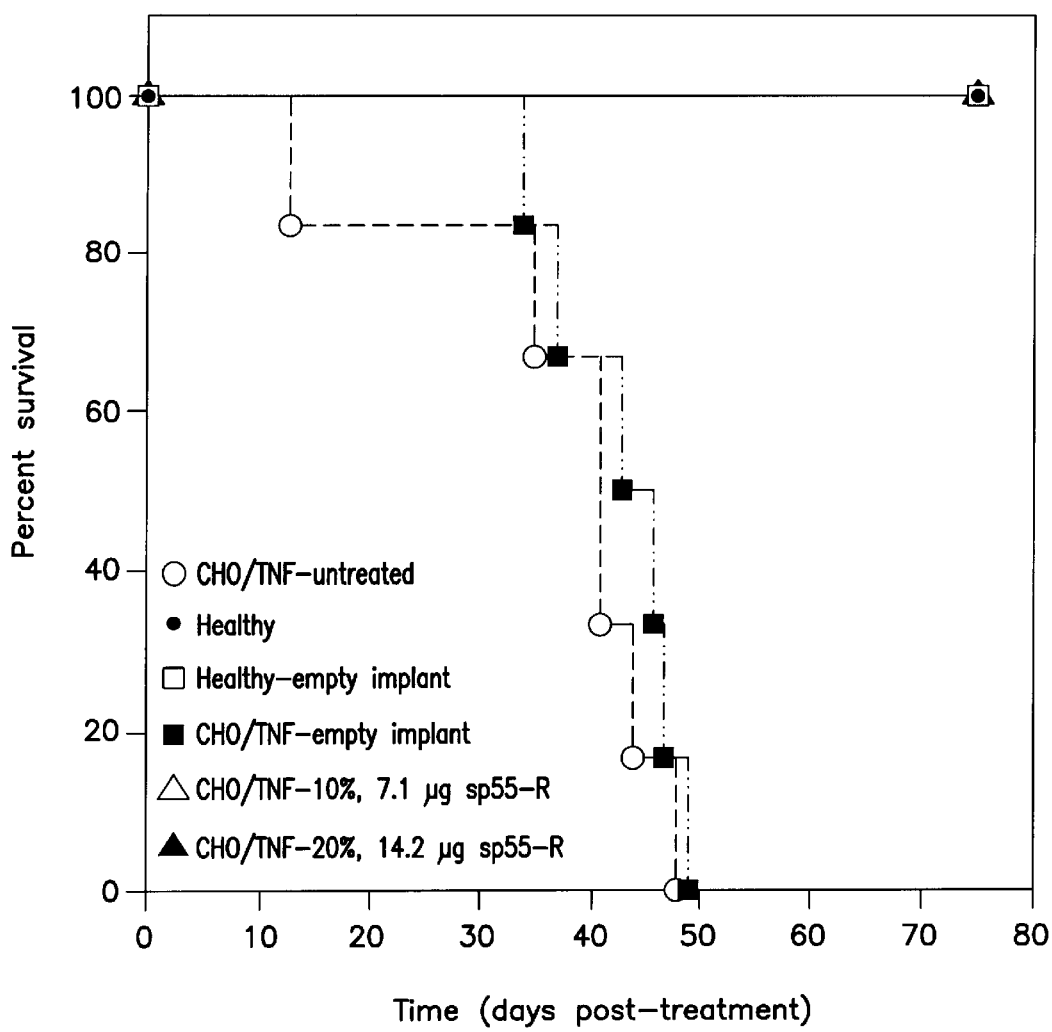
FIG. 15 shows the effect of injection of formulas of the invention on the mortality of healthy and tumor-bearing mice.

Similarly, FIG. 15 shows the survival rate for various groups of tumor-bearing mice. Only those tumor-bearing mice which were untreated (○) or treated with empty PLGA formulation (■) died over the course of the experiment; tumor-bearing mice injected with formulations containing sp55-R($\Delta$ and ▲, 10% wt. % polymer and 20 wt. % polymer, respectively, relative to glycofurol), healthy mice injected with empty formulation (□), and healthy mice which did not receive injections (●), all survived the test period.

Example 11

Degradation of Implants in PBS

Figure 17:
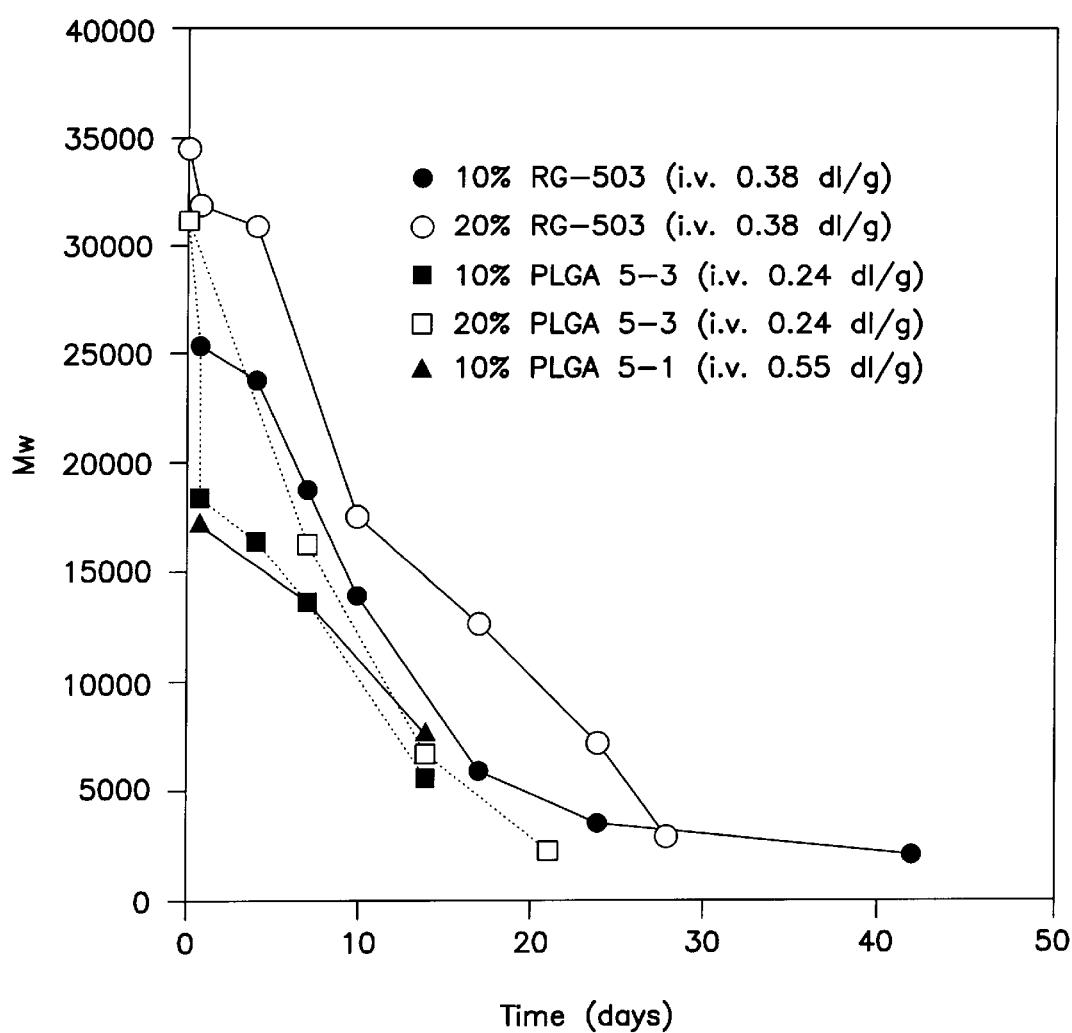
FIG. 17 shows the rate of dissolution of implants formed according to the invention (10 or 20 wt. % polymer relative to glycofurol, 1:1 weight ratio LA/GA units) as determined by gel permeation chromatography (GPC)

Implants were prepared in vitro by direct injection into PBS (pH 7.4) of 200 mg of formulations containing 10 or 20 wt. % polymer (inherent viscosity 0.38, 0.24, or 0.55 dl/g) relative to glycofurol, with a 1:1 ratio of LA to GA units. The implants thus formed were maintained at 37° C. on a shaker bath, and then dried under vacuum at various intervals for use in gel permeation chromatography (GPC). The average molecular weight of the implants was determined using a Waters 510 pump with a Waters RI-410 refractive index detector. Tetrahydrofuran (THF) was use for the mobile phase, at a flow rate of 1 ml/min and temperature of 30° C. Implants were dissolved in THF (0.25 wt. % polymer sample in THF), filtered and then injected as a 20 $\mu$l same into a set of four $\mu$-Styragel columns (Waters) with nominal pore sizes of $10^{-5}$, $10^{-6}$, $10^{-7}$, and $10^{-8}$ m. Average molecular weights were calculated using a series of polystyrene standards which ranged from 162 to 194000 molecular weight (Mw). The results are shown in FIG. 17.

Example 12

Degradation of Implants in PBS

Figure 18:
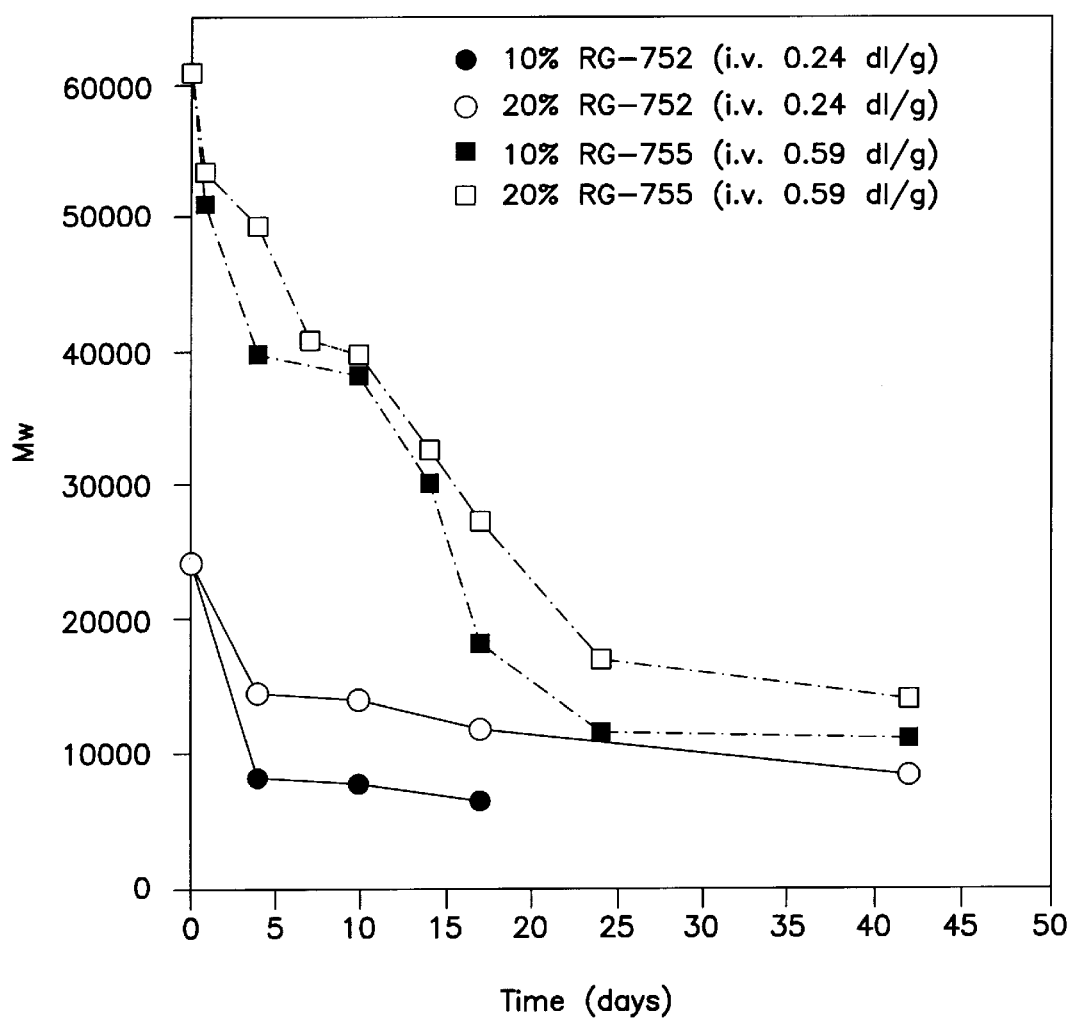
FIG. 18 is similar to FIG. 17, but shows the results for implants containing a 3:1 weight ratio LA/GA units.

The procedure of Example 11 was followed, but the implants were prepared from formulations containing PLGA (inherent viscosities of 0.24 and 0.59 dl/g) containing a 3:1 ratio of LA to GA units. The results are shown in FIG. 18.

The foregoing examples are given for illustrative purposes only. Within the scope of the invention, many modifications on the foregoing can be made. For example, small organic molecules, peptides, polypeptides, oligo- or polynucleotides, in various concentrations, can be incorporated into the solution; the average molecular weight of the polymer can be varied; the relative amounts of lactic acid and glycolic acid units can be varied; and the relative amounts of polymer and solvent can be varied, all without exceeding the scope of the invention.

What is claimed is:

1. A composition comprising a mixture of
a polymer which is poly(lactic-co-glycolic acid) copolymer (PLGA) containing between about 10 and 100 wt. % lactic acid (LA) units, and
α-(tetrahydrofuranyl)-ω-hydroxypoly(oxy-1,2-ethandiyl) (glycofurol).

2. A composition according to claim 1, said composition being a solution comprising a polymer which is poly(lactic-co-glycolic acid) copolymer (PLGA) containing between about 10 and 100 wt. % lactic acid (LA) units, said polymer being dissolved in α-(tetrahydrofuranyl)-ω-hydroxypoly(oxy-1,2-ethandiyl) (glycofurol).

3. A composition according to claim 1, further comprising a biologically active molecule from the group comprising proteins, polypeptides, peptides, organic molecules, oligo- or polynucleotides, or other biologically active molecules.

4. A composition according to claim 1, wherein the polymer has an average molecular weight between 2,000 and 100,000.

5. A composition according to claim 1, wherein the polymer has an intrinsic viscosity between 0.2 and 7.0 dl/g.

6. A composition according to claim 1, wherein the weight ratio of glycofurol to polymer is between 99:1 and 1:1.

7. A composition according to claim 6, wherein the weight ratio of glycofurol to polymer is between 9:1 and 7:3.

8. A composition according to claim 3, wherein the weight ratio of the polymer to the biologically active molecule is between 10000:1 and 1:1.

9. Use of a composition according to claim 1 in the preparation of a prosthetic or orthodontic implant.

10. A composition according to claim 1 for use in the preparation of a prosthetic or orthodontic implant.

11. Use of a composition according to claim 1 in the preparation of a device for the controlled and/or sustained release of one or more drugs or other biologically active molecules.

12. A composition according to claim 1 for use in the preparation of a device for the controlled and/or sustained release of one or more drugs or other biologically active molecules.

13. A method for producing a solid implant in situ in an animal body, including man, comprising the steps of:
a—dissolving a polymer which is poly(lactic-co-glycolic acid) copolymer (PLGA) containing from about 10–100 wt. % lactic acid (LA) units, in α-(tetrahydrofuranyl)-ω-hydroxypoly(oxy-1,2-ethandiyl) (glycofurol) to form a liquid;
b—administering a suitable amount of said liquid to an animal, including man, in need thereof, and
c—allowing said glycofurol to dissipate in said animal to leave a solid implant composed of a PLGA polymeric matrix.

14. The method of claim 13, wherein said composition in liquid form further comprises a biologically active molecule selected from the group comprising proteins, polypeptides, peptides, organic molecules, oligo- or polynucleotides, or other biologically active molecules.

15. The method of claim 13, wherein said administering of said liquid is accomplished by injection through a needle.

16. The method of claim 13, wherein the weight ratio of glycofurol to polymer prior to administration is between 99:1 and 1:1.

17. The method of claim 13, wherein the polymer has an average molecular weight between 2,000 and 100,000.

18. The method of claim 13, wherein the polymer has an inherent viscosity between 0.2 and 7.2 dl/g.

19. The method of claim 14, wherein the weight ratio of said polymer to said biologically active molecule prior to administration is between 10000:1 and 1:1.

20. A method of treating an animal, including man, in need of a prosthetic or orthodontic implant comprising the steps of:
a—dissolving a polymer which is poly(lactic-co-glycolic acid) copolymer (PLGA) containing between about 10–100 wt. % lactic acid (LA) units, in α-(tetrahydrofuranyl)-ω-hydroxypoly(oxy-1,2-ethandiyl) (glycofurol) to form a liquid;
b—administering said liquid to an animal body; and
c—allowing said glycofurol to dissipate to leave a solid implant in said animal body.

21. A method of treating an animal, including man, in need of controlled or sustained release of a drug or other biologically active agent, comprising the steps of:
a—dissolving a polymer which is poly(lactic-co-glycolic acid) copolymer (PLGA) containing between about 10–100 wt. % lactic acid (LA) units, and dissolving, dispersing or suspending said drug or other biologically active agent, in α-(tetrahydrofuranyl)-ω-hydroxypoly(oxy-1,2-ethandiyl) (glycofurol) to form a liquid, wherein said dissolving, dispersing or suspending of said drug or other biologically active agent may take place previously, concurrently, or subsequently to said dissolving of said polymer;
b—administering said liquid to an animal body; and
c—allowing said glycofurol to dissipate to leave a solid, controlled-release device in said animal body.

22. A solid implant, whenever prepared by the method of claim 13.

23. A solid implant, whenever prepared from a composition according to claim 1.

24. A method according to claim 21, whereby to produce a solid, controlled release device which releases said drug or which releases said drug or biologically active agent by diffusion, erosion or a combination of diffusion and erosion as said device degrades in said animal body.

25. The method of claim 24, wherein said implant is formed in a periodontal pocket in said body.

26. A solid, controlled release device whenever prepared by the method of claim 21.

* * * * *